(12) United States Patent
Golden et al.

(10) Patent No.: US 10,113,168 B2
(45) Date of Patent: Oct. 30, 2018

(54) RIBOZYME WITH TRNA SYNTHETASE ACTIVITY AND METHODS OF MANUFACTURING AND USING THE SAME

(71) Applicant: Purdue Research Foundation, West Lafayette, IN (US)

(72) Inventors: Barbara L. Golden, West Lafayette, IN (US); Ji Chen, West Lafayette, IN (US); Andrej Luptak, Irvine, CA (US)

(73) Assignees: Purdue Reasearch Foundation, West Lafayette, IN (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/209,422

(22) Filed: Jul. 13, 2016

(65) Prior Publication Data
US 2016/0348108 A1    Dec. 1, 2016

Related U.S. Application Data

(60) Provisional application No. 62/166,680, filed on May 27, 2015.

(51) Int. Cl.
| C12N 15/113 | (2010.01) |
| C12P 19/32  | (2006.01) |
| C12P 21/00  | (2006.01) |
| C12P 19/34  | (2006.01) |

(52) U.S. Cl.
CPC .......... *C12N 15/113* (2013.01); *C12P 19/34* (2013.01); *C12P 21/00* (2013.01); *C12N 2310/12* (2013.01); *C12N 2310/128* (2013.01)

(58) Field of Classification Search
None
See application file for complete search history.

(56) References Cited

PUBLICATIONS

Lee et al., Ribozyme-catalyzed tRNA aminoacylation, Nature Structural Biol., 2000, 7, 28-33.*
Ramaswamy et al., Designer Ribozymes: Programming the tRNA Specificity into Flexizyme, J. Am. Chem. Soc., 2004, 126, 11454-55.*
Andronescu et al., RNA STRAND: The RNA Secondary Structure and Statistical Analysis Database, BMC Bioinformatics, 2008, 9, 340.*
Zhang et al., Structure and mechanism of the T-box riboswitches, WIREs RNA, 2015, 6, 419-33.*

* cited by examiner

*Primary Examiner* — Robert B Mondesi
*Assistant Examiner* — Todd M Epstein
(74) *Attorney, Agent, or Firm* — Reichel Stohry LLP; Natalie J. Dean; Mark C. Reichel

(57) ABSTRACT

Ribozymes exhibiting tRNA synthetase activity and substrate specificity, as well as methods for engineering and producing the same, are disclosed. The ribozymes of the present disclosure comprise a T-box RNA module fused with a flexizyme module. The flexizyme module provides high promiscuity with respect to amino acid substrates and the T-box module provides tRNA substrate specificity. Systems are also described for aminoacylation of suppressor tRNAs with unnatural amino acids (uAAs), such systems comprising the ribozyme previously mentioned, suppressor tRNA, and the desired uAAs. Methods for incorporating a uAA into a growing polypeptide chain using the ribozyme hereof are also provided.

5 Claims, 13 Drawing Sheets

Specification includes a Sequence Listing.

FIG. 4B  FIG. 4C

SEQUENCE LISTING

```
<160> NUMBER OF SEQ ID NOS: 2

<210> SEQ ID NO 1
<211> LENGTH: 190
<212> TYPE: RNA
<213> ORGANISM: Artificial sequence
<220> FEATURE:
<223> OTHER INFORMATION: A fusion of a naturally occurring RNA sequence
      from Geobacillus kaustophilus and a circularly-permuted artificial
      flexizyme comprising an active site for binding an unnatural amino
      acid and able to aminoacylate a tRNA molecule

<400> SEQUENCE: 1
gagucgcgau gacggaucaa uaguaguuaa cccucucuuc cgaagcgagc cggggggcggu      60 gggagcccgg ugaagacggu uaaugaaacg gcaguccgga gcgaacauga cgaaaguggg     120
ugcgcguuug gcgcaucaag auccccgcau ccccgaaagg guacauggcg uuagguaaaa     180
aaaagggauc                                                            190

<210> SEQ ID NO 2
<211> LENGTH: 51
<212> TYPE: RNA
<213> ORGANISM: Artificial sequence
<220> FEATURE:
<223> OTHER INFORMATION: A circularly-permuted artificial flexizyme
      comprising an active site for binding an unnatural amino acid and
      able to aminoacylate the 3'-end of a tRNA molecule by reacting it
      with the unnatural amino acid

<400> SEQUENCE: 2 gaucccccgca uccccgaaag gguacauggc guuagguaaa aaaagggau c               51
```

RIBOZYME WITH TRNA SYNTHETASE ACTIVITY AND METHODS OF MANUFACTURING AND USING THE SAME

PRIORITY

This application is related to and claims priority benefit of U.S. Provisional Patent Application Ser. No. 62/166,680 to Golden et al., filed May 27, 2015. The entire content of the aforementioned priority application is hereby incorporated by reference in its entirety into this disclosure.

BACKGROUND

Proteins perform a vast array of functions within living organisms and are the chief actors within a cell. Examples of such functionality include catalyzing metabolic/chemical reactions (i.e. enzymes), cell signaling and signal transduction, DNA replication, providing structural support (i.e. structural proteins), and transporting molecules from one location to another. Proteins differ from one another primarily with respect to their sequence of amino acids, which is dictated by the nucleotide sequence of their genes and typically results in protein folding into a specific three-dimensional (3D) structure that determines its activity.

In basic ribosomal protein biosynthesis, messenger RNA (mRNA) encodes a protein through the process of translation. In brief, ribosome molecules read down the length of mRNA codons (each a sequence of three-nucleotides) and translate the genetic information contained therein to a specific sequence of amino acids by facilitating complementary base pairing to the complementary transfer RNA (tRNA) anticodons.

Each mRNA codon is recognized by a particular tRNA. During translation, each of the tRNA molecules that bind the mRNA is "charged," meaning that it is carrying a specific amino acid via a covalent bond. As such, when a particular tRNA binds with its complementary codon on the mRNA at the ribosome, its cargo amino acid is lined up with the amino acid of the tRNA corresponding to the next codon on the mRNA. Thereafter, a peptide bond forms between the amino acids and the tRNA releases its amino acid, thus forming a chain of amino acids—or a polypeptide—as the mRNA pass through and are read by the ribosome. Termination of the polypeptide happens when the ribosome hits a stop codon in the mRNA that ends the translation process. The polypeptide is released and folds into its dictated 3D geometry. Accordingly, the specific nucleotide sequence of an mRNA specifies which amino acids are incorporated into the protein product, with the role of tRNA being to specify which amino acids correspond with the sequence from the mRNA. The particular sequence of amino acid in a protein product has a direct effect as to the resulting structure and, thus, functionality of the protein.

Conventionally, each type of tRNA molecule can be attached to only one type of amino acid. The covalent attachment between the tRNAs and their specific amino acids is catalyzed by aminoacyl tRNA synthetases. Typically, aminoacyl tRNA synthetases are extremely specific with respect to tRNA and the related amino acid. Accordingly, a specific tRNA substrate will only take on a particular amino acid when aminoacylated with the correct aminoacyl tRNA synthetase Through protein engineering techniques, the natural translation process can be manipulated to study protein structure and function, as well as for protein modification. Indeed, protein engineering has become an extensively used tool in molecular biology, with methods for incorporating even unnatural amino acids (uAAs) into proteins to develop unique functionalities and/or improved protein function. For example, the site-specific introduction of uAAs can be used to probe enzyme mechanisms, increase acidity, localize proteins within cells (through adding a fluorescent label or otherwise), improve the therapeutic properties of drugs, and the like. Because of the potential in this area, there is significant interest in expanding the chemical diversity of proteins beyond the twenty (20) amino acids most commonly incorporated during ribosomal protein synthesis.

The most common conventional method of introducing an uAA during protein biosynthesis employs a functional pair of tRNA and aminoacyl tRNA synthetase ("ARS")—an orthogonal set—to act independently of the endogenous aminoacylation machinery of the cell. Specifically, the ARS is engineered to charge a tRNA (for example, an amber suppressor tRNA) with the particular uAA of interest while the tRNA recognizes a specialized codon within the mRNA (typically an amber STOP codon (UAG, for example) or a four-base codon) that does not code for one of the natural amino acids. Accordingly, the charged tRNA delivers the uAA to the ribosome for protein synthesis and, in doing so, uniquely introduces the uAA into a protein at the desired site.

To be introduced selectively at its predetermined position only, the orthogonal set must not crosstalk with the endogenous tRNA and synthetase sets, while remaining functionally compatible with the ribosome and other components of the translation apparatus. This is problematic for several reasons, one of which being that many tRNA synthetases recognize the anticodon loop of the tRNA and thus cannot be used to charge a tRNA that recognizes a stop codon. Furthermore, the active site of the ARS must be capable of accommodating the uAA of interest. As proteins normally have exquisite specificity for their substrates, this can significantly limit the identity of the uAA accepted.

Orthogonal tRNA synthetases are conventionally generated using archaeal proteins that, when introduced into prokaryotes such as *E. coli*, can discriminate between all of the tRNA substrates available in a cell or in an in vitro translation system and bind only to its orthogonal tRNA partner. In this manner, only the appropriate tRNA substrate is charged with the uAA. However, Eukarya is the most complex domain of life, with not only more tRNA gene content, but also higher variation. So while conventional orthogonal methodologies have had some success in prokaryotic and in vitro translation systems, a robust mechanism to introduce uAAs into eukaryotes has yet to be established. Indeed, the foreign ARS and tRNA conventional pairs are typically not successful when used in vivo in eukaryotic cells, as there is a substantial risk the orthogonal set will recognize—and charge—their homologs derived from the host organism. Furthermore, as previously stated, significant engineering is required to redesign the orthogonal ARS such that it will accept the uAA, and each desired modification within a protein potentially requires additional engineering of the ARS.

Accordingly, what is needed is an efficient and effective system capable of selecting and selectively charging tRNA with a wide variety of uAAs within a eukaryotic cell.

BRIEF SUMMARY

The present disclosure provides artificial ribozymes comprising a T-box element and a flexizyme (an amino-acylating ribozyme) and methods for producing the same. Also disclosed are methods for incorporating an unnatural amino acid into a protein using the novel artificial ribozymes described herein.

In at least one exemplary embodiment of the present disclosure, an artificial ribozyme is provided, the ribozyme comprising a T-box element and a flexizyme. The flexizyme comprises an active site for binding an unnatural amino acid and charging a tRNA molecule through a CCA-tail at its 3'-terminus, and the T-box element recognizes and preferentially binds the body of a tRNA substrate. Furthermore, the flexizyme is linked with the T-box element such that the flexizyme can bind and aminoacylate a tRNA substrate bound by the T-box element. The T-box element of the ribozyme may be linked to the flexizyme through a P1 stem of the flexizyme. Additionally or alternatively, the active site of the flexizyme is not specific to a targeted unnatural amino acid.

In at least one exemplary embodiment, the T-box element may be a bacterial T-box element derived from a Geobacillus kaustophilus and the flexizyme may comprise a dinitro-flexizyme. Furthermore, the flexizyme may comprise a circular permutation formed by a link between an original 3'-terminus end of the flexizyme and an original 5'-terminus end of the flexizyme, wherein a P1 loop of the flexizyme is open to create a new 5'-terminus end and a new 3'-terminus end and comprises SEQ ID NO. 2. In some embodiments of the aforementioned circular permutation, the original 5'-terminus end and the original 3'-terminus end of the flexizyme may be joined by a linker comprised of seven, eight, or ten nucleotides. Alternatively, the flexizyme may comprise a linear permutation formed by a link between a 3'-terminus end of the T-box element and a 5'-terminus end of the flexizyme, there the link comprising a poly-A linker comprising between five and ten nucleotides. Still further, the ribozyme may comprise SEQ ID No. 1 and/or a 3'-terminus of the T-box element may be linked to a 5'-terminus of a circularly permuted flexizyme such as that shown in SEQ ID NO. 2.

Methods for producing an artificial ribozyme are also provided. In at least one embodiment, the method comprises the steps of: attaching a 3'-terminus end of a T-box element with a 5'-terminus end of a circularly-permuted flexizyme such that the flexizyme can aminoacylate a tRNA substrate that is bound by the T-box element; binding, with specificity, an anticodon of a preferred tRNA substrate with a specifier loop of the T-box element; binding a 3'-terminus end of the preferred tRNA substrate with an acceptor end of the flexizyme; and aminoacylating the preferred tRNA substrate with an unnatural amino acid bound to an active site of the flexizyme. Additional embodiments of the methods described herein may further comprise the step of optimizing a rate at which the step of aminoacylating the preferred tRNA substrate is performed by modifying a discriminant base of the 3'-terminus end of the preferred tRNA substrate to complement a base of the acceptor end of the flexizyme. Additionally or alternatively, the methods may further comprise the step of modifying a binding specificity of the T-box element by adding or removing base pairs from a P1 stem of the flexizyme. Still further, certain embodiments comprise the step of modifying aminoacylation efficiency of the flexizyme by adding or removing base pairs from a P1 stem of the flexizyme.

Methods for incorporating an unnatural amino acid into a protein are also disclosed. In at least one embodiment, the method comprises the steps of: providing an artificial ribozyme, a preferred tRNA substrate, and an unnatural amino acid substrate to a translation system, the translation system comprising translation components derived from a bacterial, archeaeal, or eukaryotic organism and the ribozyme comprising: a binding element with specificity for binding a preferred tRNA substrate, and a catalytic element linked to the binding element, the catalytic element for catalyzing aminoacylation of a tRNA substrate bound by both the binding element and the catalytic element, and the catalytic element comprising an active site for binding an unnatural amino acid; binding, with specificity, an anticodon of the preferred tRNA substrate with the binding element of the ribozyme; binding a 3'-terminus end of the preferred tRNA substrate with the catalytic element of the ribozyme; reacting the catalytic element with the preferred tRNA substrate under conditions such that an unnatural amino acid substrate bound to the active site of the catalytic element is released and a bond is formed between the preferred tRNA substrate and the amino acid substrate to produce a charged tRNA; and producing a protein, wherein the unnatural amino acid is incorporated into the protein.

In at least one embodiment of the above-described method, the step of providing further comprises delivering the artificial ribozyme, the preferred tRNA substrate, and an amino acid substrate to a cell on a single plasmid. Additional embodiments comprise the step of releasing the charged tRNA from the artificial ribozyme. In certain embodiments, the T-box element of the ribozyme is orthogonal with respect to the translation components derived from the bacterial, archeael, or eukaryotic organism and/or the preferred tRNA substrate may be a suppressor tRNA. Furthermore, the cell may be from an organism including, without limitation, a cell selected from the group consisting of a bacterial cell, a yeast cell, an insect cell, and a mammalian cell, and the method is performed in vivo.

Additionally or alternatively, the preferred tRNA substrate may be provided in a pool of variant tRNA substrates and the method step of binding, with specificity, an anticodon of the preferred tRNA substrate may further comprise selecting the preferred tRNA substrate from a pool comprising the preferred tRNA substrate and endogenous tRNA substrates. There, the pool may also further comprise one or more aminoacyl synthetase/tRNA pairs, where the tRNA of such pair(s) are not the preferred tRNA substrate.

BRIEF DESCRIPTION OF THE SEQUENCE LISTING

SEQ ID NO. 1 is an RNA sequence of at least one exemplary embodiment of a ribozyme according to the present disclosure, such ribozyme having tRNA synthetase activity:

5'-GAGUCGCGAUGACGGAUCAAUAGUAGUUAACCCUCUCUUCCGAAGCG

AGCCGGGGCGGUGGGAGCCCGGUGAAGACGGUUAAUGAAACGGCAGUCC

GGAGCGAACAUGACGAAAGUGGGUGCGCGUUUGGCGCAUCAAGAUCCCCG

CAUCCCCGAAAGGGUACAUGGCGUUAGGUAAAAAAAAGGGAUC-3';

and

SEQ ID NO. 2 is an artificial sequence of at least one exemplary embodiment of a circularly permuted flexizyme according to the present disclosure, such flexizyme comprising an active site for binding an unnatural amino acid and able to charge a tRNA molecule with the unnatural amino acid:

5'-GAUCCCCGCAUCCCCGAAAGGGUACAUGGCGUUAGGUAAAAAAAGGG
AUC-3'.

In addition to the foregoing, a written Sequence Listing for the above-described artificial sequences is appended hereto and the same Sequence Listing is provided in computer readable form encoded in a file filed herewith and herein incorporated by reference. The information recorded in computer readable form is identical to the written Sequence Listing provided herein, pursuant to 37 C.F.R. § 1.821(f).

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 2 illustrates a T-box riboswitch binding a tRNA, with subpart (A) illustrating that when the tRNA is charged with an amino acid, there is no transcription and the gene is turned off and subpart (B) illustrating that when the tRNA is uncharged, it interacts with the antiterminator helix and the gene is turned on;

FIGS. 4B and 4C show the sequences and secondary structure models of an unmodified dFx flexizyme module (FIG. 4B) and at least one embodiment of the circularly permuted flexizyme (FIG. 4C) disclosed herein, comprising SEQ ID NO. 2, and used to generate the ribozyme of FIGS. 3B and 4A;

Figures 1A, 1B:
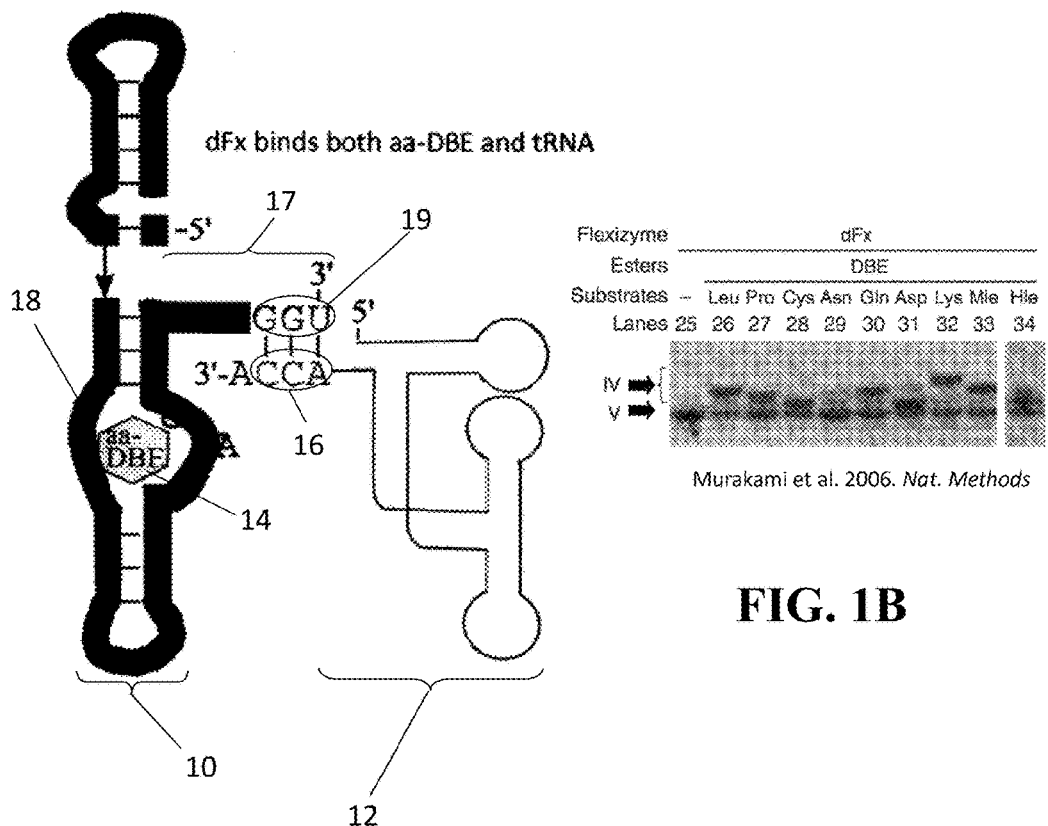
FIG. 1A illustrates the binding of a tRNA and an activated amino acid (dintrobenzyl ester (DBE) by a flexizyme.
FIG. 1B shows a gel displaying the results of charging a tRNA with a variety of amino acids using the flexizyme of FIG. 1A.

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Various techniques and mechanisms of the present disclosure will sometimes describe a connection or link between two components. Words such as attached, linked, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. Consequently, a connection does not necessarily mean a direct, unimpeded connection unless otherwise noted.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Thus, for example, reference to "a tRNA" includes a combination of two or more tRNAs; reference to "bacteria" includes mixtures of bacteria, and the like.

As used herein, the term "orthogonal" refers to a molecule (e.g., an orthogonal tRNA and/or an orthogonal aminoacyl tRNA synthetase) that is intended to function with endogenous components of a cell with reduced efficiency as compared to a corresponding molecule that is endogenous to the cell or translation system, or that fails to function with endogenous components of the cell.

As used herein, the term "cognate" means components that function together, for example, a tRNA and aminoacyl tRNA synthetase that preferentially aminoacylates that tRNA. These components can also be referred to as being "complementary."

As used herein, the phrase "selector codon" refers to a codon recognized by an orthogonal tRNA in a translation process that is not typically recognized by an endogenous tRNA. Typical examples include stop codons, codons comprising four (4) or more bases, and/or the like. An orthogonal-tRNA anticodon loop recognizes a selector codon, e.g., in an mRNA, and inserts its amino acid into a polypeptide being translated by translation system components. For example, in at least one embodiment herein, the tRNA recognizes a selector codon such as an amber STOP codon and adds an uAA into a polypeptide being produced by the translation process. Selector codons can include, for example and without limitation, nonsense codons (such as STOP codons, e.g., amber, ochre, and opal codons), four (4) or more base codons, rare codons, codons derived from natural or unnatural base pairs, and/or the like.

As used herein, the phrase "suppressor tRNA" is a tRNA that alters the reading of a mRNA in a given translation system, for example, by providing a mechanism for incorporating an amino acid into a polypeptide chain in response to a selector codon. By way of a non-limiting example, a suppressor tRNA can read through a stop codon, a four (4) base codon, a rare, codon, etc.

As used herein, the phrase "translation system" refers to the components that incorporate an amino acid into a growing polypeptide chain (protein). Components of the translation system can include, for example, ribosomes, tRNAs, synthetases, mRNA, and the like. The novel tRNA and/or tRNA synthetases of the present disclosure can be added to or be part of an in vitro or in vivo translation system, for example, in a non-eukaryotic cell (e.g., a bacterium such as *E. coli*) or in a eukaryotic cell (e.g., a mammalian cell, a plant cell, a yeast cell, an algae cell, a fungus cell, an insect cell, and/or the like) or an organism.

As used herein, the phrase "unnatural amino acid" or related abbreviation "uAA" refers to any amino acid, modified amino acid, and/or amino acid analogue that is not one of the twenty (20) common naturally occurring amino acids or the rare natural amino acids.

As used herein, the phrase "derived from" refers to a component that is isolated from or made using a specific molecule or organism, or information from the specific molecule or organism.

As used herein, the term "encodes" refers to any process whereby the information in a polymeric macromolecule or sequence string is used to direct the production of a second molecule or sequence string that is different from the first molecule or sequence string. As used herein, the term is used broadly and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase. In another aspect, the term "encode" refers to any process whereby the information in one molecule is used to direct the production of a second molecule that has a different chemical nature from the first molecule. For example, as is well known in the art, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

As used herein, the term "riboswitch" refers to a regulator segment of a mRNA molecule commonly found in the 5'-untranslated region, that binds another molecule (e.g., metabolites or metal ions as ligands) and regulates mRNA or protein expression by forming alternative structures in response to this ligand binding.

As used herein, the terms "T-box" and "T-box RNA" refer to a naturally occurring riboswitch that recognizes a cognate tRNA through interaction with the anticodon loop of that tRNA and can control gene expression (i.e. toggles it on or off) based on whether the aminoacyl group on the tRNA is present, i.e. the tRNA is charged.

As used herein, the term "leader" refers to a wild-type or variant form of the upstream portion of a bacterial gene, particularly a bacterial gene that is regulated by a T-box termination/antitermination complex, and that comprises the elements of a T-box termination/antitermination complex, including a specifier sequence, a T-box, and conserved terminator and antiterminator consensus motifs.

"glyQS," as used herein, refers to either a DNA molecule that comprises all or a portion of a bacterial glyQS gene (including the promoter and leader regions), and optionally all or a portion of the polynucleotide coding sequence encoding a wild-type or variant bacterial glycyl-tRNA synthetase, or an mRNA product encoded by the same.

"Gram positive bacteria," as used herein, means the phylogenetic group of bacteria commonly known as and referred to as the Gram-positive branch.

As used herein, the term "ribozyme" refers to RNA molecules that are capable of catalyzing specific biochemical reactions. Within the ribosome, ribozymes activities function as part of the large subunit ribosomal RNA to link together amino acids during protein synthesis to form protein chains.

As used herein, the term "flexizyme" refers to an artificial ribozyme that catalyzes the aminoacylation of tRNA with a chemically synthesized amino acid substrate. Flexizymes can accept a wide variety of amino acid substrates with diverse functional groups, opposite chirality, etc., but do not conventionally recognize tRNA with any specificity.

In order to generate a protein that contains a synthetic or unnatural amino acid (uAAs) therein, as previously described, conventional methods require the use of orthogonal pairs of an aminoacyl tRNA (ARS) and a tRNA that can function efficiently in the translational machinery, but that are "orthogonal" to the translation system at issue, meaning that the pairs function independently of the synthetases and tRNAs endogenous to the translation system itself. Desirable characteristics of the orthologous pair include tRNA that decode or recognize only a specific new codon, e.g., a selector codon, that is not decoded by any endogenous tRNA, and an ARS that preferentially aminoacylates (or charges) its cognate tRNA with only a specific amino acid. The orthogonal tRNA is also desirably not aminoacylated by endogenous synthetases. Generating such orthogonal pairs requires extensive engineering and often results in low or unsuccessful yields, especially in vivo in eukaryotes.

Here we report a novel artificial ribozyme molecule that is capable of both discriminating between tRNA molecules and effectively charging a cognate tRNA with an uAA in vitro and potentially in vivo in prokaryotes, archaea, and eukaryotes alike. To achieve this, the compositions and methods of the present disclosure uniquely combine the highly promiscuous nature of flexizymes with respect to amino acids and a tRNA-recognition module from T-box RNA. The resulting ribozyme results in a composition that can encode amino acids with specified codons in vivo without the use of conventional orthogonal pairs, adds specificity to traditional flexizyme characteristics in that it can both aminoacylate—or charge—tRNA with a wide variety of amino acid substrates (including chemically synthesized uAAs), does not require reengineering if a different amino acid substrate is used, and also exhibits significant specificity for a cognate tRNA (with determinants for tRNA recognition involving both the discriminator base and the anticodon of tRNA). Moreover, because it is an RNA molecule, the inventive ribozyme hereof can be delivered to a cell on a single plasmid along with its cognate tRNA substrates. As such, there is no need to translate the catalyst into a protein as is commonly seen in conventional systems.

Now referring to FIG. 1A, a conventional flexizyme 10 bound to both a tRNA 12 and an amino acid 14 (here, amino acid dintrobenzyl ester) is shown for comparative purposes. Generally, a flexizyme 10 is an artificial ribozyme that catalyzes the aminoacylation of tRNA with a uAA or other amino acid 14. In relevant part, flexizymes 10 generally have a core composed of one irregular and three A-form helices, with the irregular helix comprising an active site 18 (or moiety binding pocket) for interacting with and/or binding amino acids 14. A hairpin bend near the 3'-terminus of the flexizyme 10 forms an acceptor stem 17 that allows the terminal three (3) nucleotides at the acceptor end 19 (GGU) to protrude away from the helical stack and makes them available for base pairing to the cytosine-cytosine-adenine (CCA)-terminus 16 of an tRNA substrate 12 (or other CAA sequences as described below).

The activity of flexizymes is not restricted by the functional group of the amino acid substrate, but, as stated above, its acceptor end 19 binds and acts on the CCA sequence 16 at the 3'-terminus end of the tRNA substrate 12. As CCA sequences 16 at the 3'-terminus end is a feature consistent across tRNA substrates, flexizymes 10 lack the ability to discriminate a cognate tRNA from noncognate tRNA. Accordingly, flexizymes 10 aminoacylate any tRNA substrate 12 with which it comes into contact. While this highly promiscuous nature is advantageous in that flexizymes can accept a wide variety of amino acid substrates with diverse functional groups and subsequently aminoacylate a tRNA substrate 12 with the same, it ultimately renders flexizymes 10 ineffective for cotranslationally incorporating uAAs (or other amino acids) into proteins using in vitro or in vivo translation systems. Indeed, for such systems to be effective, the aminoacyl synthetase used (or ARS-like ribozyme) must specifically bind one particular tRNA (such as, for example, an amber suppressor tRNA).

Figure 2:
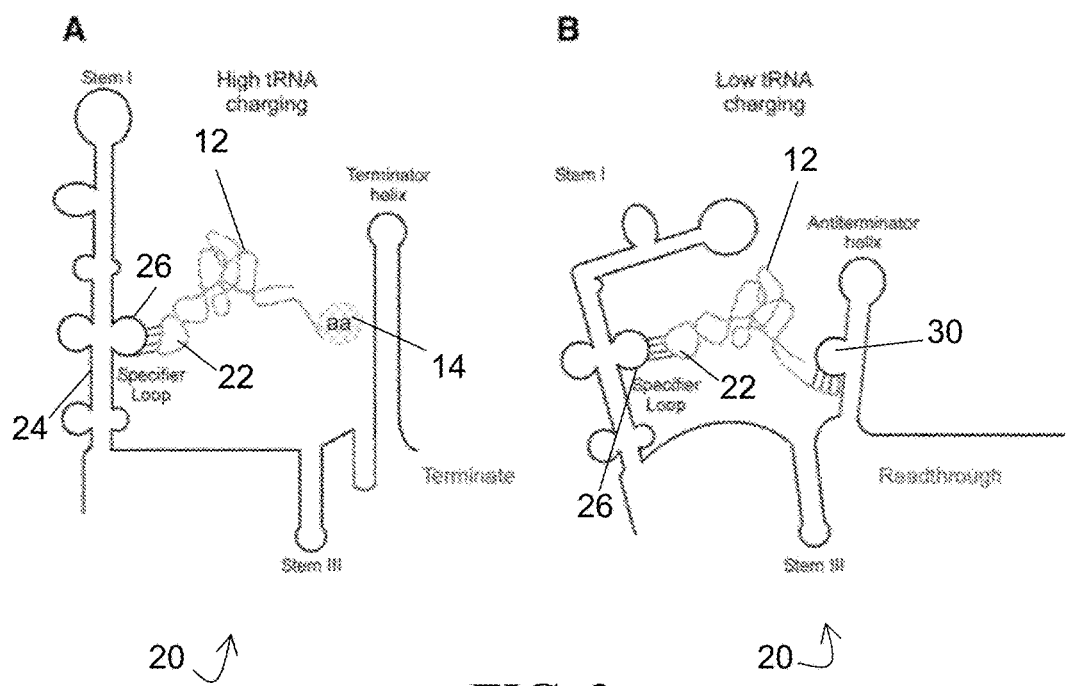

T-box RNAs 20, on the other hand, are naturally occurring riboswitches that can recognize a cognate tRNA through interaction with the anticodon loop 22 of the tRNA 12. Examples of the T-box mechanism are illustrated in FIG. 2, subparts (A) and (B), shown bound to tRNA 12 (both aminoacylated (subpart (A)) and uncharged (subpart (B))) for reference. The T-box mechanism regulates the expression of aminoacyl tRNA synthetase (ARS)-related genes in gram-positive bacteria. In this system, a riboswitch element in the upstream or "leader" region 24 of the nascent transcript monitors the relative amounts of charged versus uncharged species of a specific tRNA through direct binding of tRNA 12 by the leader RNA 24 at the specifier loop 26 thereof. Perhaps more specifically, binding a specific uncharged tRNA to a riboswitch element causes a structural change in the transcript that promotes expression of the downstream coding sequence.

As shown in subpart (B) of FIG. 2, when bound, uncharged tRNA 12 interact at both the specifier loop 26 (via anticodon loop 22 of the tRNA 12) and, at its acceptor end 27, with the bulged region in the antiterminator 30 as shown in subpart (B) of FIG. 2. This dual interaction stabilizes the antiterminator 30 and prevents the formation of a competing terminator helix, thereby enabling transcription to read through the termination site and into the downstream coding sequence. Conversely, when an aminoacylated tRNA 12 binds the T-box RNA 20, the presence of the amino acid 14 prevents interaction of the acceptor end 27 of the tRNA 12 with the antiterminator 30, thus ending transcription.

Unlike flexizymes, T-box RNA exhibit tRNA specificity at both of its binding sites and, as such, recognize the anticodon 22 and the CCA tail of cognate tRNA 12. Indeed, recognition of the tRNA 12 by the leader 24 may mimic recognition by an aminoacyl tRNA synthetase, which often exploits the anticodon 22 and discriminator 15 positions as specificity determinants.

Figure 3A:
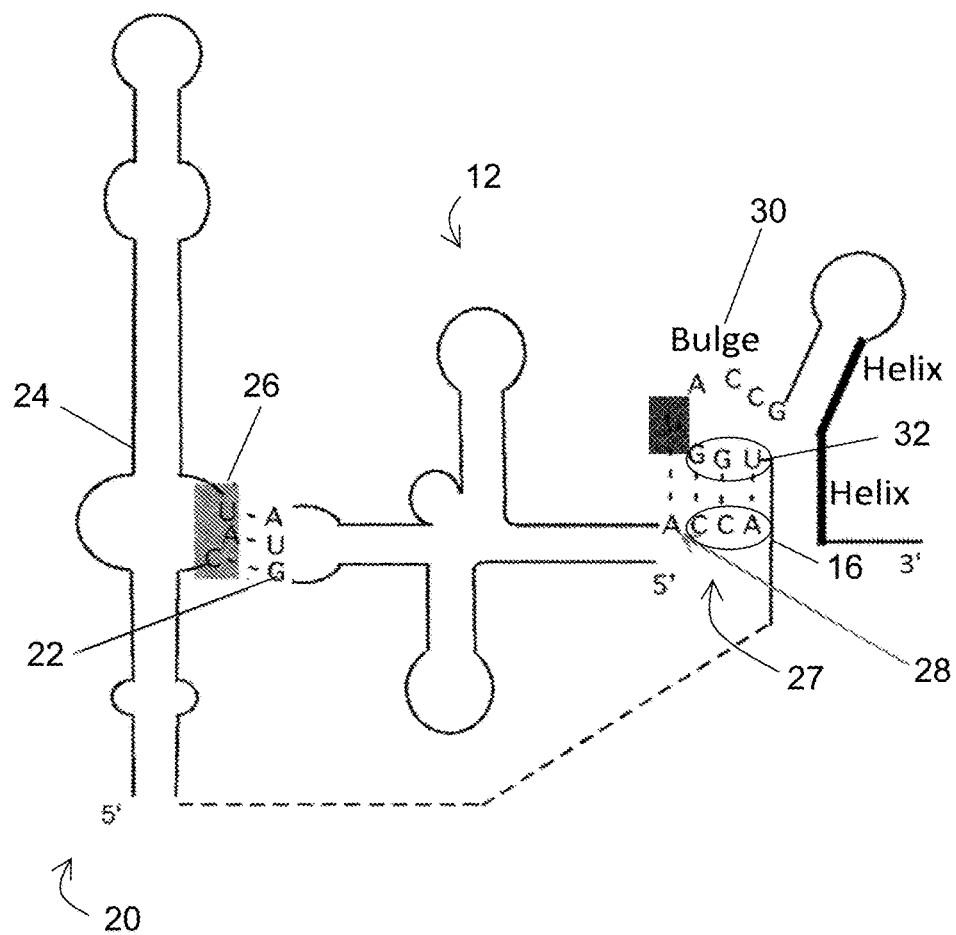
FIG. 3A illustrates the recognition of the anticodon and CCA tail of the tRNA by the T-box RNA.

FIG. 3A illustrates an alternative view of an uncharged tRNA 12 bound with a T-box RNA 20 that shows additional detail of the tRNA acceptor end 27 and T-box antiterminator 30 interaction. As shown in FIG. 3A, if the tRNA 12 is uncharged, the CCA-tail 16 at the 3'-terminus end of the bound tRNA 12 can base pair with the UGG sequence 32 upstream of the T-box riboswitch in a manner reminiscent of the interaction between the flexizyme 10 and a CCA-tail 16 of its substrate tRNAs 12 (see FIG. 1A). Notably, FIG. 3A also illustrates discriminator base 28, which will be referenced in further detail below in connection with T-box RNA 20 specificity.

Figure 3B:
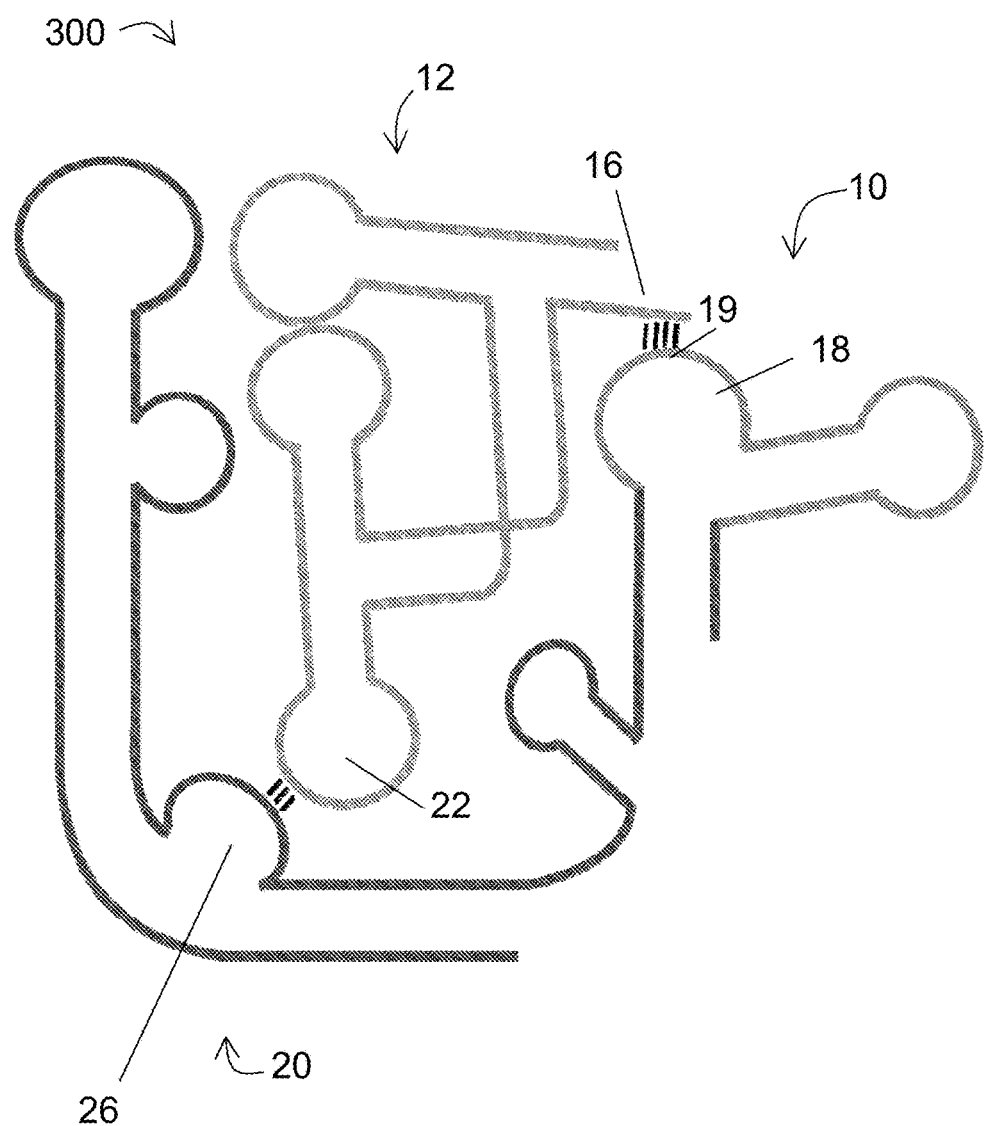
FIG. 3B illustrates a model of interaction of the elements of at least one embodiment of a ribozyme of the present disclosure.

Expanding from this identified interaction and its similarities with conventional flexizymes, the concept of building the catalytic activity of a flexizyme into T-box RNA was developed. In at least one embodiment of the present disclosure, a fusion ribozyme 300 is provided. FIG. 3B provides a high-level view of the conceptual interaction between the components of the fusion ribozyme 300. Generally, the fusion ribozyme 300 comprises catalytic/flexizyme module 10 linked and/or fused together with a T-box RNA module 20. The catalytic/flexizyme module 10 comprises a molecule based on a flexizyme and, as described herein, will hereinafter be referred to as the "flexizyme module."

Both the flexizyme and T-box modules 10, 20 are capable of interacting with a tRNA 12, with the flexizyme module 10 catalyzing the aminoacylation thereof with a desired amino acid substrate 14 and the T-box module 20 providing a degree of tRNA 12 specificity. For example and as previously described, the acceptor end 19 of the flexizyme module 10 interacts with a CCA-tail 16 of a tRNA 12 and the T-box module 20 comprises at least a tRNA binding domain (specifier loop) 26 capable of interacting with the anti-codon 22 of a cognate tRNA substrate 12. Furthermore, as the flexizyme module 10 also comprises an active site 18 for binding an amino acid 14 for aminoacylation of the tRNA substrate 12. In this manner, when the fusion ribozyme 300 hereof is used in protein engineering and cotranslation techniques, it can select a specific tRNA 12 and charge it with a wide variety of amino acids 14 (artificial or otherwise) without any reengineering.

Various embodiments of the fusion ribozyme 300 are provided herein, the structures and variations of which will now be described in additional detail. Now referring to FIG. 4A, at least one exemplary embodiment of a ribozyme 400 is shown. The ribozyme 400 comprises a flexizyme module 100 fused with a T-box module 200 as described in connection with fusion rib ozyme 300.

Figure 4A:
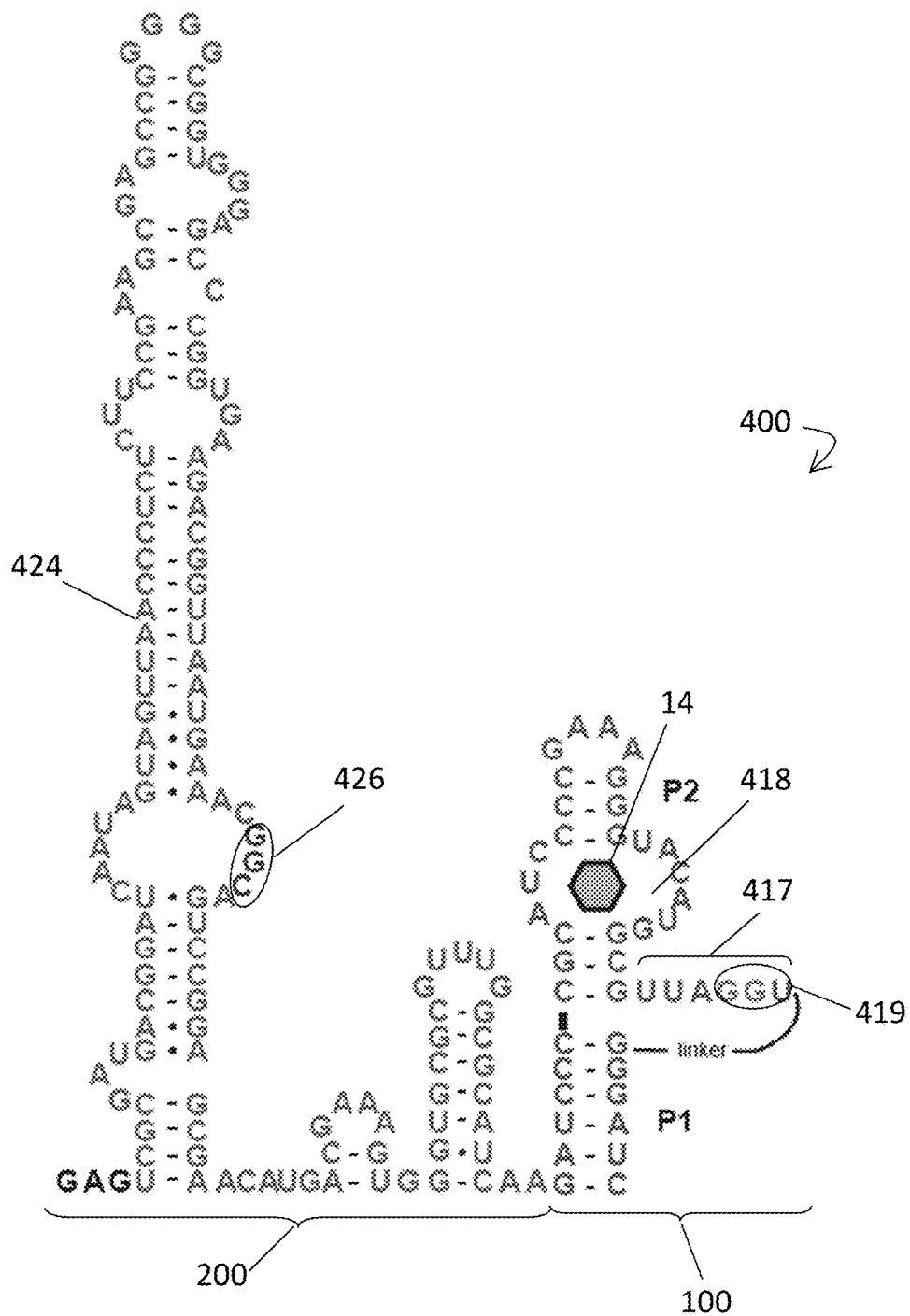
FIG. 4A shows the sequence and secondary structure model of at least one exemplary embodiment of the ribozyme comprising SEQ ID NO. 1 of FIG. 3B.

FIG. 4A shows that the T-box and flexizyme modules 200, 100 of the ribozyme 400 are linked through the P1 stem of the flexizyme module 100. The resulting ribozyme 400 exhibits both exemplary tRNA-synthetase activity and significant specificity for a cognate tRNA. While the flexizyme module 100 of the ribozyme 400 may comprise any suitable type of flexizyme 100 now known or hereinafter developed (including, for example and without limitation, Fx3 or any of its variants), in this at least one exemplary embodiment, the flexizyme module 100 starts with dinitro-flexizyme (dFx). To create the ribozyme 400 of the present disclosure, the crystal structure of a T-box riboswitch 200 bound to a cognate tRNA 12 is employed, and the acceptor stem 27 of the bound tRNA 12 is superposed with acceptor stem analog 417 present in the crystal structure of the flexizyme 100, for example, Fx3, dFx, or the like. As described herein, the particular embodiment of the ribozyme 400 wherein the flexizyme module 100 comprises dFx is termed "STARzyme," which is representative of the name "specific tRNA aminoacylating rib ozyme" and comprises SEQ ID NO. 1.

Notably, for the ribozyme 400 to be effective at recognizing the anticodon 22 of a tRNA 12 and performing a chemical reaction at the acceptor stem 417 of the flexizyme 100, the orientation of the T-box module 200 with respect to the flexizyme module 100 should preferably be optimized. Indeed, through several iterative rounds of design, it was determined that a circular permutation of the flexizyme 100 and optimization of both the linker length and length of the connector helix can have a significant effect on the ribozyme's 400 specificity for a cognate tRNA 12. Accordingly, in at least one exemplary embodiment of the ribozyme 400, the flexizyme module 100 comprises a circular permutation of dFx (SEQ ID NO. 2). In such embodiments, the circularly permuted dFx module 100 may comprise seven (7), eight (8), or ten (10) nucleotide linkers 450 (see FIG. 4F). In the exemplary STARzyme embodiment, the flexizyme module 100 comprises a circular permutation of dFx and an eight (8) nucleotide linker.

FIG. 4A illustrates detail regarding the structure of a ribozyme 400, in at least one embodiment where the T-box module 200 comprises a tRNA$^{Gly}_{GCC}$ specific T-box (glyQS T-box) from Geobacillus kaustophilus (Gkau) and the flexizyme module 100 comprises a circularly permuted version of the aminoacylating ribozyme dFx. The Gkau glyQS T-box has a relatively minimal structure, is thermodynamically stable, and the crystal structure is readily available for reference; all characteristics that are beneficial in the current context. Notwithstanding the foregoing example, it will be understood that while dFx and the Gkau glyQS T-box (and other flexizymes and/or T-box RNAs) are used herein to describe the various embodiments of the present disclosure, such examples are not intended to be limiting. Indeed, any appropriate flexizyme and/or T-box RNA may be used in connection with the novel ribozymes and related methods of the present disclosure, provided that, in at least certain embodiments, the T-box riboswitch and flexizyme selected do not bump or overlap when fused as described herein. This may be tested and/or confirmed with 3D modeling, activity assays, and/or similar techniques.

For comparison purposes, FIGS. 4B and 4C, respectively, show the flexizyme 100 (here, dFx, with FIG. 4C comprising SEQ ID NO. 2) in its linear and circular permutated versions. The T-box RNA 200 comprises nucleotides 426 for anticodon recognition (FIG. 4A) and flexizyme 100 comprises nucleotides 428 for binding the CAA tail 16 of a cognate tRNA bound to the T-box module 200 (not shown). In the at least one embodiment shown in FIG. 4A, the sequence GAG was also added to the 5'-end of the ribozyme 400 to facilitate efficient in vitro transcription of the ribozyme by T7 RNA polymerase; it is not required for ribozyme activity.

Finally, flexizyme 100 further comprises an active site 418 for binding the designated amino acid 14 (including, without limitation, a uAA). This model demonstrates that the T-box riboswitch 200 and the flexizyme 100 do not sterically interfere with each other when docked to a tRNA and, as such, support their combined use in an engineered ribozyme 400 with tRNA-synthetase activity (see FIG. 1, subpart (A), in particular).

The results indicate that the flexizyme 1000 (here, dFx) charged tRNA$^{Gly}_{GCC}$ with $k_{obs}$=0.2±0.040 h$^{-1}$. In comparison, the flexizyme 100 charged tRNA$^{Ile}_{GAU}$ with $k_{obs}$=0.6±0.080 h$^{-1}$ (see Table 1), a 3-fold, and statistically significant, difference.

TABLE 1

Kinetic parameters for dFx and STARzymes. Parameters reported herein represent average values from the three independent measurements. Errors stand for standard deviations.

| Ribozyme construct | $k_{obs}$ (h$^{-1}$), tRNA$^{Gly}_{GCC}$ U73A (cognate) | $f_{max}$, tRNA$^{Gly}_{GCC}$ U73A (cognate) | $k_{obs}$ (h$^{-1}$), tRNA$^{Ile}_{GAU}$ | $f_{max}$, tRNA$^{Ile}_{GAU}$ | $k_{obs}$ (h$^{-1}$), tRNA$^{Gly}_{GCC}$ | $f_{max}$, tRNA$^{Gly}_{GCC}$ | $k_{obs}$, cognate/ $k_{obs}$, tRNA$^{Ile}_{GAU}$ | $k_{obs}$, cognate/ $k_{obs}$, tRNA$^{Gly}_{GCC}$ |
|---|---|---|---|---|---|---|---|---|
| dFx | 0.54 ± 0.082 | 0.75 ± 0.016 | 0.60 ± 0.080 | 0.80 ± 0.047 | 0.20 ± 0.041 | 0.86 ± 0.0099 | 0.90 | 2.7 |
| STAR-A8 | 0.21 ± 0.015 | 0.57 ± 0.0077 | 0.055 ± 0.0032 | 0.50 ± 0.015 | 0.067 ± 0.015 | 0.50 ± 0.15 | 3.8 | 3.1 |
| STAR-A8-minus1 | 0.16 ± 0.0066 | 0.55 ± 0.0061 | 0.047 ± 0.0094 | 0.40 ± 0.044 | 0.065 ± 0.017 | 0.44 ± 0.072 | 3.4 | 2.5 |
| STAR-A10 | 0.17 ± 0.048 | 0.55 ± 0.021 | 0.090 ± 0.029 | 0.52 ± 0.13 | 0.085 ± 0.012 | 0.45 ± 0.041 | 1.9 | 2.0 |
| STAR-A7 | 0.092 ± 0.015 | 0.49 ± 0.095 | 0.026 ± 0.0061 | 0.46 ± 0.15 | 0.034 ± 0.0061 | 0.52 ± 0.057 | 3.5 | 2.7 |

Figure 4D:
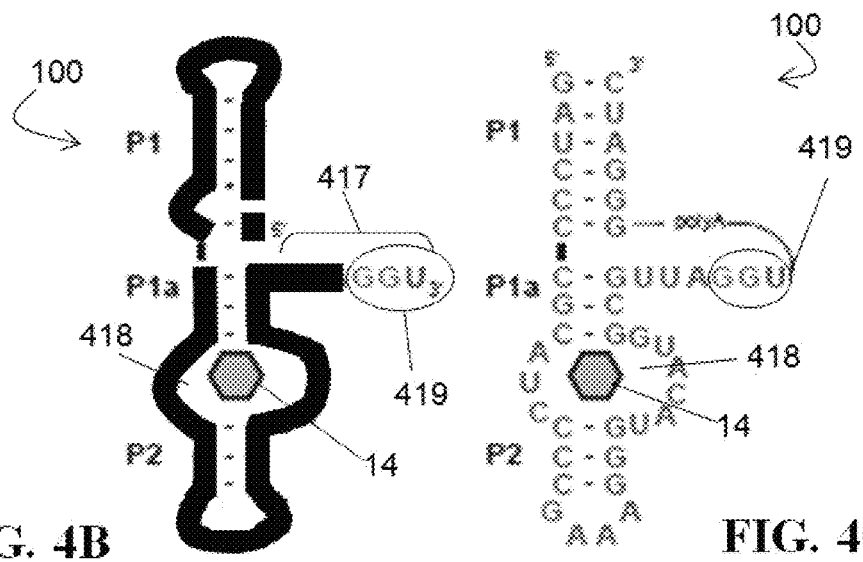
FIG. 4D shows a three-dimensional model of the ribozyme of FIG. 4A bound to a cognate tRNA (tRNA$^{Gly}_{GCC}$), with the flexizyme module comprising a Fx3 flexizyme and the T-box comprising a glyQS T-box.
Figure 4D:
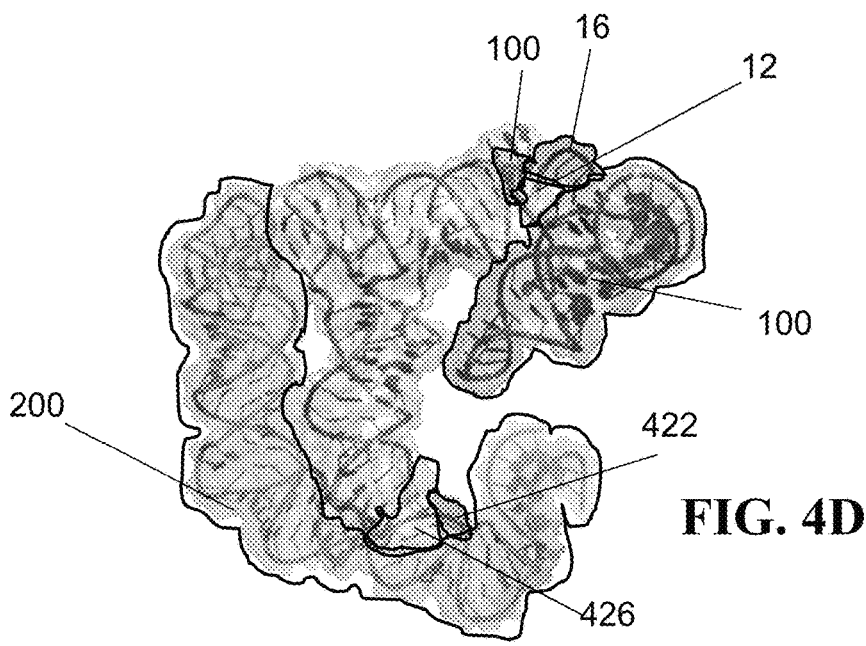

Now referring to FIG. 4D, a 3D image of a starting model for tRNA recognition by the ribozyme 400 is shown (PDB ID 4 MGN and 3CUL). As per FIG. 4D, the visible portions of the ribozyme 400 comprise stem I of the T-box module 200 (here, glyQS), a bound cognate tRNA 12 (here, tRNA$^{Gly}_{GCC}$), the flexizyme module 100 (here, Fx3), a specifier loop 426 of the T-box RNA 200, an anticodon 422 of the tRNA substrate 12, and the CAA tail 16 from a superposed acceptor stem analog 417 within the flexizyme 100 structure (with the remainder of the acceptor stem analog 417 structure not shown for the sake of simplicity). At least in this embodiment, stems II and III of the T-box module 200 were not specifically modified, with the spacer region enabling the tRNA to bind both stem 1 and the antiterminator region.

Figure 4E:
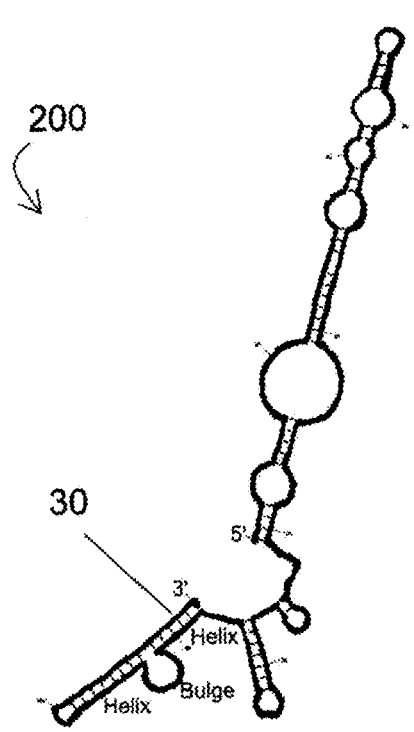
FIGS. 4E and 4F illustrates a comparison between the secondary structure models of a glsQS T-box (FIG. 4E) and the ribozyme of FIG. 4A (FIG. 4F)
Figure 4F:
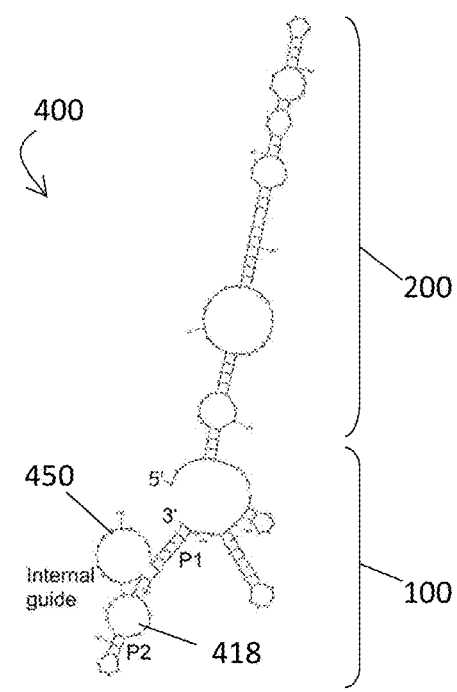

FIGS. 4E and 4F provide a side-by-side comparison of how closely the structure of the fusion ribozyme 400 (here, illustrated as being tRNA$^{Gly}$-specific) of the present disclosure mimics a glyQS T-box with respect to the antiterminator topology.

In support of the novel principles and compositions set forth herein, several studies were performed on the ribozymes 300, 400 hereof to confirm and optimize their novel functionality.

Figure 5:
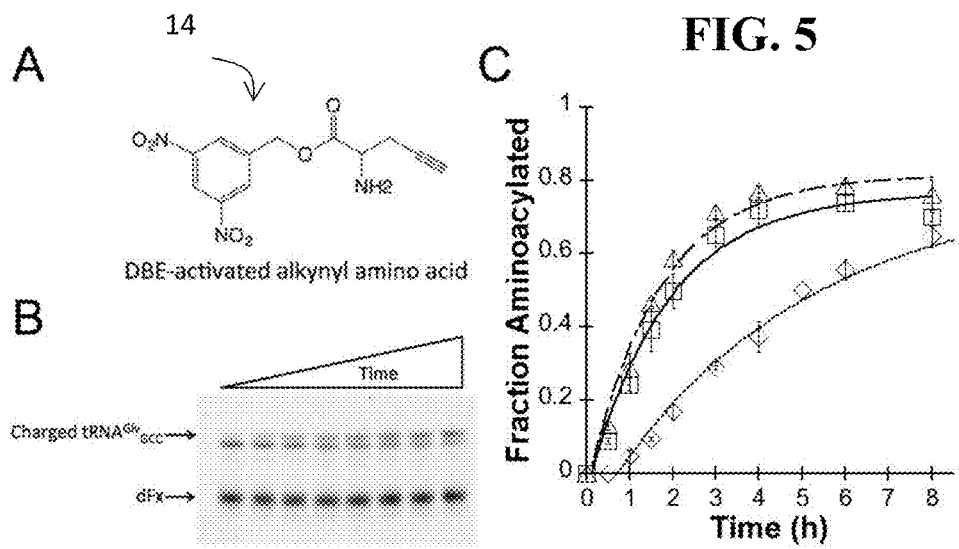
FIG. 5 show results of a single-turnover kinetics study for dFx, with subpart (A) showing the 3,5-dinitrobenzyl ester (DBE)-activated alkynyl amino acid substrate used in the study; subpart (B) showing a representative gel image showing the accumulation of the slower-migrating band (charged tRNA$^{Gly}_{GCC}$) over time (gel stained with SYBR Green II); subpart (C) showing a graph of a reaction progress curve for dFx against tRNA$^{Gly}_{GCC}$ U73A mutant (open square), tRNA$^{Gly}_{GCC}$ (open diamond), or tRNA$^{Ile}_{GAU}$ (open triangle)
Figure 6:
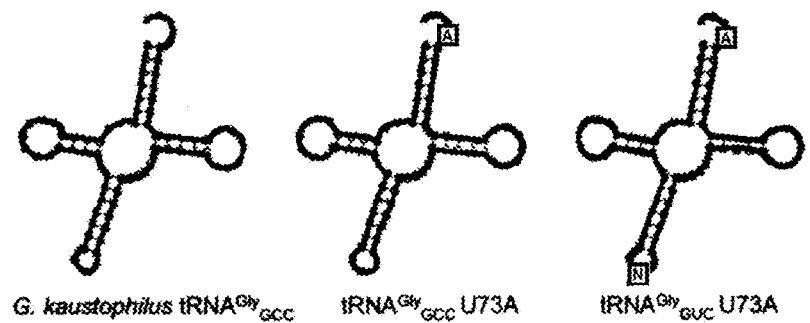
FIG. 6 illustrates the sequences and secondary structures of tRNA constructs used in connection with the studies described in the present disclosure, with mutations highlighted with boxes.
Figure 6:
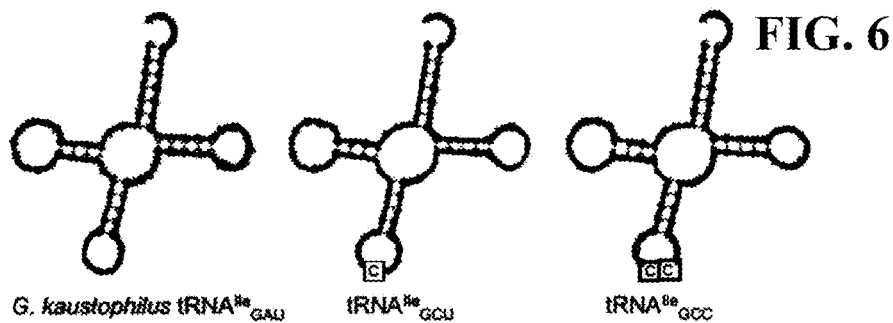

The Isolated dFx Flexizyme Exhibits Specificity for the Discriminator Base of tRNA To verify that the ribozyme 400 (and, in particular, the isolated flexizyme 100 thereof) exhibits the desired specificity for the discriminator base 28 of the tRNA 12 when the T-box riboswitch 200 and the flexizyme 100 are fused, the catalytic activity of the flexizyme 100 as it relates to specific tRNA substrates 12 was tested in connection with an activated amino acid substrate carrying an alkynyl group (see FIG. 5, subpart (A)). Perhaps more specifically, the observed rate constant ($k_{obs}$) of aminoacylation reaction on both tRNA$^{Gly}_{GCC}$ and tRNA$^{Ile}_{GAU}$ substrates were measured through single-turnover kinetic assays (see FIG. 5, subparts (B) and (C)) (e.g., mix 10 µM of refolded ribozyme 400 with 2 µM of refolded tRNA; add saturating akynyl-DBE to initiate the reaction; incubate the reaction at 4° C. and take aliquots at desired time points; and perform acid gel electrophoresis followed by SYBR-green II staining). The sequence and secondary structure of the tRNA substrates used are shown in FIG. 6, with mutations (where applicable) highlighted by boxes.

It is known that aminoacylation is most productive when the discriminator base 28 at position 73 immediately preceding the CCA-tail of the tRNA 12 is complementary to the 3'-terminal U of Fx3 (which is equivalent to U46 in dFx). tRNA$^{Ile}_{GAU}$ has a discriminator base A and can form a Watson-Crick base pair with U46 of dFx, while tRNA$^{Gly}_{GCC}$ has as U at the discriminator base position 28 and therefore cannot make a base pair with U46 of dFx when used as the flexizyme 100. Accordingly, the variation between the $k_{obs}$ values observed in connection with the specificity tests is consistent with the previous study where aminoacylation yields were compared between tRNAs having different discriminator bases 28.

In view of this, additional tests were performed to ascertain if the reactivity variation observed between the two tRNAs was accurately attributable to the difference in discriminator base 28 or some other factor. In furtherance of this, a U73A mutation was introduced into tRNA$^{Gly}_{GCC}$ (see FIG. 6). This mutation rescued the ribozyme activity ($k_{obs}$=0.54±0.080 for tRNA$^{Gly}_{GCC}$ U73A mutant versus $k_{obs}$=0.60±0.080 h$^{-1}$ for tRNA$^{Ile}_{GAU}$), thus indicating that U-to-A mutation restores flexizyme 100 activity (at least when the flexizyme comprises dFx) and supporting discriminator base 28 specificity.

FIG. 5, subpart (C) displays reaction progress curves for dFx against tRNA$^{Gly}_{GCC}$ U73A mutant (open square), tRNA$^{Gly}_{GCC}$ (open diamond), or tRNA$^{Ile}_{GAU}$ (open triangle), as does Table 1. As maximal activity of the fusion ribozyme 400 is expected to require Watson-Crick base-pairing at both the discriminator base 28 and the anticodon loop 22 of the tRNA, the tRNA$^{Gly}_{GCC}$ U73A mutant was used as the cognate tRNA for the remaining studies.

tRNA Binding Activity of the T-box and Fusion Ribozymes

To characterize the tRNA binding properties of the T-box RNA 200 and the fusion ribozymes 400 of the present disclosure, native gel band shift assays were performed using a previously established protocol for the Gkau glyQS T-box riboswitch 200. Isolated Gkau glyQS T-box riboswitch RNA 200 was used as a positive control (labeled as "T-box") and tRNA$^{Ile}_{GAU}$ was used as a negative control (labeled as "tRNA$^{Ile}$"). A linear ribozyme 400 was created by connecting the 3'-terminus of the T-box module 200 to the 5'-terminus of the dFx module 100 via a 5- to 8-nt poly-A linker 450 (see FIG. 4F). Secondary structure prediction by Mfold supported correct folding of both modules 100, 200 within the ribozyme 400.

T-box RNA or the T-box-dFx linear ribozyme 400 was added to cognate tRNA$^{Gly}_{GCC}$ A73U or non-cognate tRNA$^{Ile}_{GAU}$. As shown in FIG. 9A, the addition of up to 6-fold molar excess of T-box or fusion RNA gradually shifted the cognate tRNA$^{Gly}_{GCC}$ A73U, thus the band corresponding to the tRNA disappeared as the riboswitch 200 or ribozyme 400 was added. (Note that no new band for the complex of tRNA with the riboswitch 200 or fusion RNA 400 was observed and, while it is not clear as to why a supershift was not observed under these conditions, it is possible the tRNA complex was smeared or comigrated with another band.) Conversely, the results clearly demonstrated that the band corresponding with the noncognate tRNA$^{Ile}_{GAU}$ remained unshifted and did not change in intensity following the addition of the riboswitch 200 or linear fusion 400. These results indicate that the T-box module 200 embedded in the fusion construct 400 is functional and that it provides the fusion ribozyme 400 with tRNA binding specificity.

Circular Permutation of dFx

The catalytic activity of the linear fusion RNA 400 was also explored using the single turnover assay previously described in connection with the dFx-ribozyme 400. While the linear ribozyme 400 was catalytically active, its activity was lower than that observed for dFx (a circular permutation). Further, the linear permutation of the flexizyme 100 did not distinguish the cognate tRNA from noncognate tRNA (data now shown). The tRNA-binding properties and the presence of catalytic activity support that the T-box and flexizyme modules 200, 100 are both folded and functional. However, the lack of discrimination and diminished catalytic activity suggest that this embodiment of the linear flexizyme module 100 cannot simultaneously bind to the CCA-tail 16 of the tRNA 12 when the tRNA 12 is docked to the T-box riboswitch module 200.

Referring back to FIG. 4D, the working 3D model of the ribozyme 400 supports that a circular permutation of the flexizyme 100 (created by linking the 5'- and 3'-terminus ends and opening the P1 loop) provides advantageous topology for fusing the two modules 100, 200 within the ribozyme 400. Although disrupting the structure of the CCA-binding site 19 on the single stranded tail at the 3'-terminus end of the flexizyme 100 is problematic as any structural disruption would be detrimental to ribozyme 400 activity, it was determined that a number of adenosines can be used to successfully link the 5'-terminus of the parental flexizyme molecule 100 with the 3'-terminus containing the CCA-binding site 19 to provide flexibility without deleterious effect (see FIG. 4B). Indeed, at least with respect to dFx flexizymes 100, this insertion did not interfere with formation of the native secondary structure.

Accordingly, in at least one exemplary embodiment of the present disclosure herein referred to as the STARzyme, the 3'-end of the glyQS T-box 200 may connect to the new 5'-end of the circularly permuted flexizyme 100 (here, dFx). As comparatively illustrated in FIGS. 4E and 4F, the overall topology of this embodiment of ribozyme 400 (FIG. 4F) resembles that of the wild-type glyQS T-box 200 (FIG. 4E), where the aptamer domain 30 is connected to a helix (A1 in the glyQS T-box and P1 in STARzyme) that is then linked to a bulge containing the binding motif for the CCA tail.

Detection of the tRNA-linked Amino Acid

While the activity assay previously described employed a gel mobility assay to monitor the aminoacylation of tRNA, further steps were performed to confirm that the shift in gel mobility was due to the addition of an uAA to the tRNA. To achieve this, covalent modification through 'click' chemistry was employed. The tRNA$^{Gly}_{GCC}$ A73U mutant was aminoacylated using a dFx flexizyme 100 (to form the STARzyme as referred to herein) for a period expected to provide the maximal yield of tRNA product. The reaction mixture was treated with Alexa Fluor 488 Picolyl Azide, which contains a fluorophore and an azide group. This reagent specifically targets the aminoacyl group on the tRNA with a fluorescent probe, which specifically labels the tRNAs that have been aminoacylated by the ribozyme 400, while the ribozyme 400 itself and unreacted product remain untouched.

Reactions and controls were divided in two and loaded side-by-side on a single polyacrylamide gel, which was subsequently cut into halves. The first half was stained with SYBR-Green II to allow for visualization of all RNA products and the second half was left unstained. The two half gels were reconstituted prior to scanning.

Figure 7:
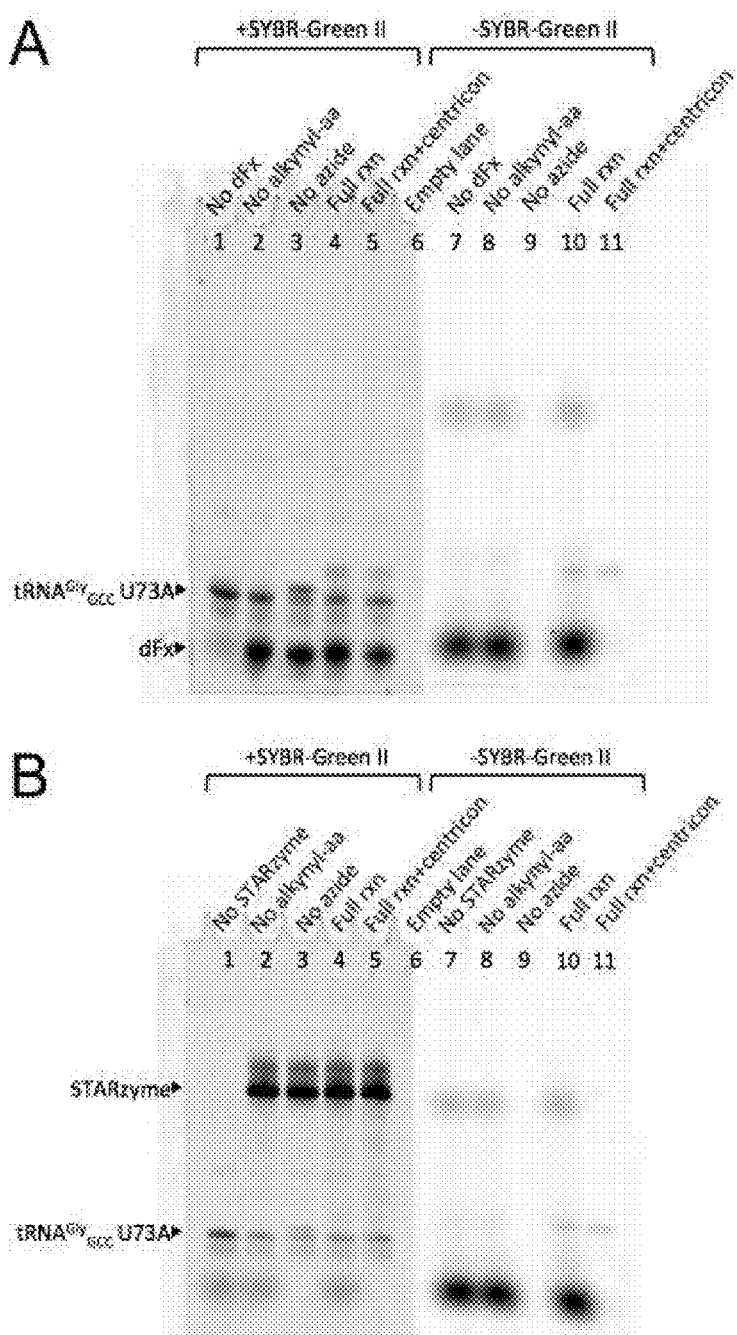
FIG. 7 shows the results of aminoacylation assays using dFx (subpart A) and STARzyme (subpart B); controls provided that have intentional omission of the following reaction components: no dFx: dFx was omitted from the aminoacylation reaction; no alkynyl-aa: the DBE-activated alkyne-containing amino acid was omitted from the aminoacylation reaction; no azide: the Alexa Fluor 488 picolyl azide was omitted from the click reaction; full rxn: all reaction components were present; full rxn+centricon: same as "Full rxn," except that the reaction sample was allowed to pass through an Amicon Ultra centrifugal filter unit with a 10 k NMWL cutoff to remove excess dye.

A fluorescently labeled band was observed at the molecular weight corresponding to the aminoacylated tRNA product only when all of the required components of the aminoacylation reaction were present within the mixture (see FIG. 7, subparts (A) and (B)). When small molecules were removed from the reaction by ultracentrifugation, only a single fluorescently labeled band—again, corresponding to the size of the aminoacylated tRNA product—was observed. This data supports that the ribozyme 400 is in fact catalyzing the addition of uAAs to a tRNA substrate 12. Note that in the SYBR-Green II stained gel, the putative reaction product (i.e. the charged tRNA) migrates higher upon the addition of Alexa Fluor 488-tagged picolyl azide. The identity of the "supershifted" band was further confirmed by the detection of Alexa Fluor 488 fluorescence in the unstained portion of the gel. Upon ultrafiltration, the single fluorescent band (lane #11) on the right half of the gel comigrates with the "supershifted" band on the left half of the gel (lane #4 or lane #5).

Optimizing the Catalytic Activity of the Ribozyme

Various variants of the ribozyme 400 may be engineered to optimize its tRNA specificity and/or catalytic activity. For example, linker 450 size has been found to contribute to tRNA specificity of the ribozyme 400. Accordingly, in at least circular permutations of the flexizyme 100, the inventive ribozyme 400 hereof may be engineered to comprise a specific number of nucleotide linkers 450 within its flexizyme module 100.

Embodiments comprising seven (7), eight (8), and ten (10) nucleotide linkers 450 in circularly permuted dFx flexizyme module 100 were analyzed for catalytic activity in the presence of either cognate or noncognate tRNAs. Again, the tRNA$^{Gly}_{GCC}$ A73U mutant is considered cognate because it can base pair with both the specifier nucleotides 426 of a T-box 200 and nucleotides at acceptor end 419 of flexizyme 100 (e.g., U46 of dFx).

An embodiment of ribozyme 400 with the flexizyme 100 comprising dFx and an eight (8) nucleotide linker 450 was only 2.6-fold less reactive than isolated dFx in the presence of the cognate tRNA. The observed rate constant for this embodiment of ribozyme 400 was about 0.21 ±0.015 h$^{-1}$, while—in comparison—isolated dFx exhibits a rate constant of 0.54±0.082 h$^{-1}$. Although the reactivity of the ribozyme 400 is slightly lower than that of the isolated dFx ribozyme 400, STAR-A8 was 3.8-fold less active in the presence of the noncognate tRNA$^{Ile}_{GAU}$ ($k_{obs}$=0.055±0.0032 h$^{-1}$) as compared to when in the presence of the cognate tRNA$^{Gly}_{GCC}$ U73A (see Table 1).

The eight (8) nucleotide linker 450 proved most advantageous—if not optimal—with respect to the ribozyme 400 gaining the most tRNA specificity as compared at least to the STARzyme with a ten (10) nucleotide linker 450, which displayed only a 1.9-fold difference in the observed rate constants for cognate and non-cognate tRNAs ($k_{obs}$=0.17±0.048 $h^{-1}$ for the cognate tRNA versus $k_{obs}$=0.090±0.029 $h^{-1}$ for tRNA$^{Ile}_{GAU}$). While the STARzyme with a seven (7) nucleotide linker 450 exhibited a similar difference in rate constants for cognate versus non-cognate tRNA ($k_{obs}$=0.092±0.015 $h^{-1}$ for the cognate tRNA versus $k_{obs}$=0.026±0.0061 $h^{-1}$ for tRNA$^{Ile}_{GAU}$), the catalytic activity of the ribozyme 400 was severely compromised (see Table 1). In sum, the difference in ribozyme 400 activity seen between the cognate tRNA$^{Gly}_{GCC}$ U73A mutant and the non-cognate tRNA$^{Ile}_{GAU}$ supports that the ribozyme 400 hereof uses the specifier nucleotides 426 in the T-box module 200 to recognize the anticodon loop 22 of the tRNA 12 and, as such, gains specificity.

In addition to studying the effect of increasing or decreasing the number of linkers 450 present within a flexizyme module 100, the discriminator base's 28 role as a specificity determinant was also assessed by characterizing the ribozyme's 400 reaction to wild-type tRNA$^{Gly}_{GCC}$. Similar to the results observed for a dFx-flexizyme 100, the STARzyme-flexizyme 100 was 2- to 3-fold less active with the wild-type tRNA$^{Gly}_{GCC}$ than with the tRNA$^{Gly}_{GCC}$ U73A mutant (Table 1). Accordingly, the ribozyme 400 clearly achieves tRNA discrimination through recognition of both the anticodon 22 and discriminator base 28 of the tRNA 12. This is clearly seen in FIG. 9B where maximal activity requires base-pairing at the anticodon (compare squares with triangles) and base-pairing at the discriminator base (compare squares with diamonds).

Figure 8:
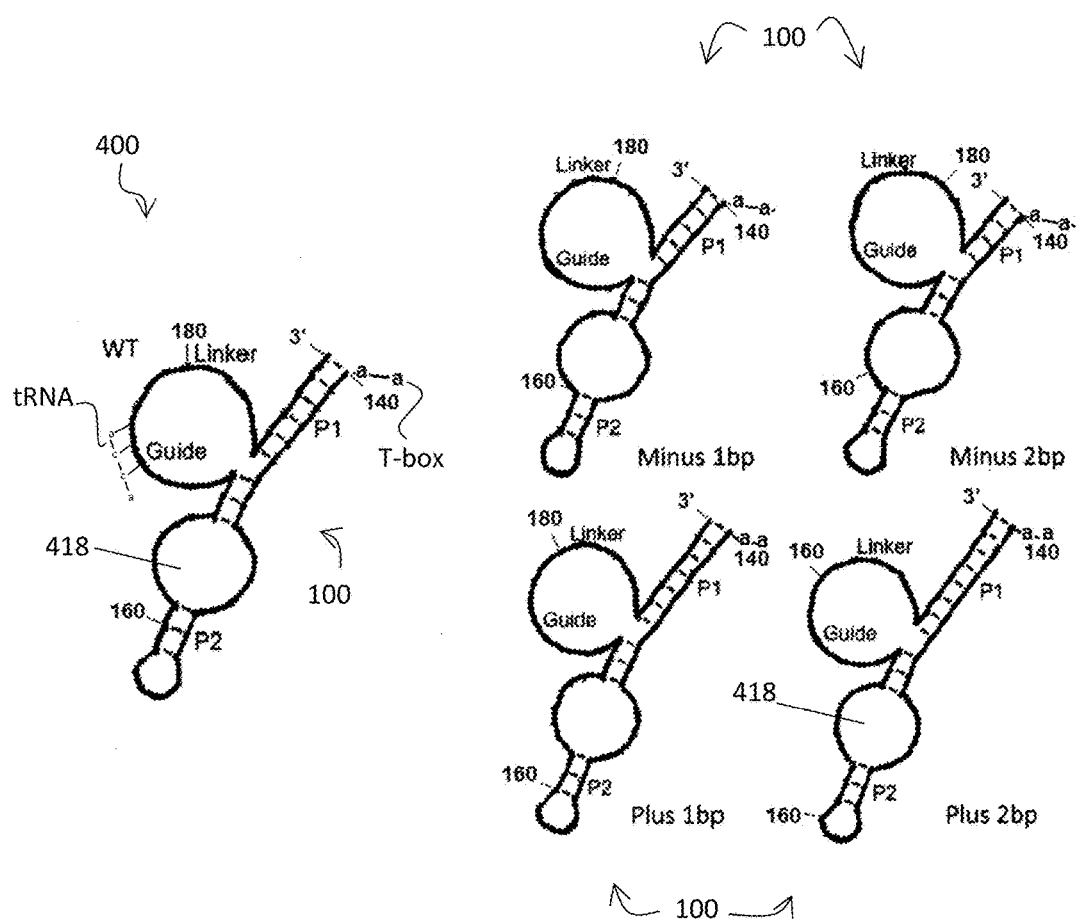
FIG. 8 shows the sequences and secondary structure models of possible flexizyme module variants that may be used in connection with embodiments of the ribozyme of the present disclosure.

Now referring to FIG. 8, the T-box and flexizyme modules 200, 100 of the fusion ribozyme 400 are linked together through the P1 stem of the flexizyme 100 (also see FIG. 4A in connection with dFx). It has been determined that changing the length of the P1 helix has a significant impact on the activity of the ribozyme 400 due to the geometrical constraints of the helix itself. Indeed, addition or removal of even a single base pair from P1 of the flexizyme module 100 as shown in FIG. 8 not only changes the length of the connector, but also the orientation of the flexizyme 100 active site 418 with respect to the T-box module 200 due to the twist of the helix. Accordingly, to ensure the interplay between the flexizyme module 100 and the T-box module 200 is optimized, the effects of mutations on non-cognate tRNA binding was assessed.

Wild-type tRNA$^{Ile}_{GAU}$ can potentially make two base pairs (one Watson-Crick and one wobble) with the specifier nucleotides 426, GCC, from the T-box module 200. The first mutant is tRNA$^{Ile}_{GCU}$, which contains a single A-to-C mutation at position 35. tRNA$^{Ile}_{GCU}$ was predicted to form two G•U wobble pairs with the specifier 426 trinucleotide GGC. The second mutant is tRNA$^{Ile}_{GCC}$, where the anticodon 22 sequence has been changed from GAU to GCC to restore the specifier-anticodon base pairing. Single-turnover kinetics were measured using these two mutants as substrates and $k_{obs}$ values were compared to those of the wild-type tRNA$^{Ile}_{GAU}$ and the cognate tRNA.

Figure 9:
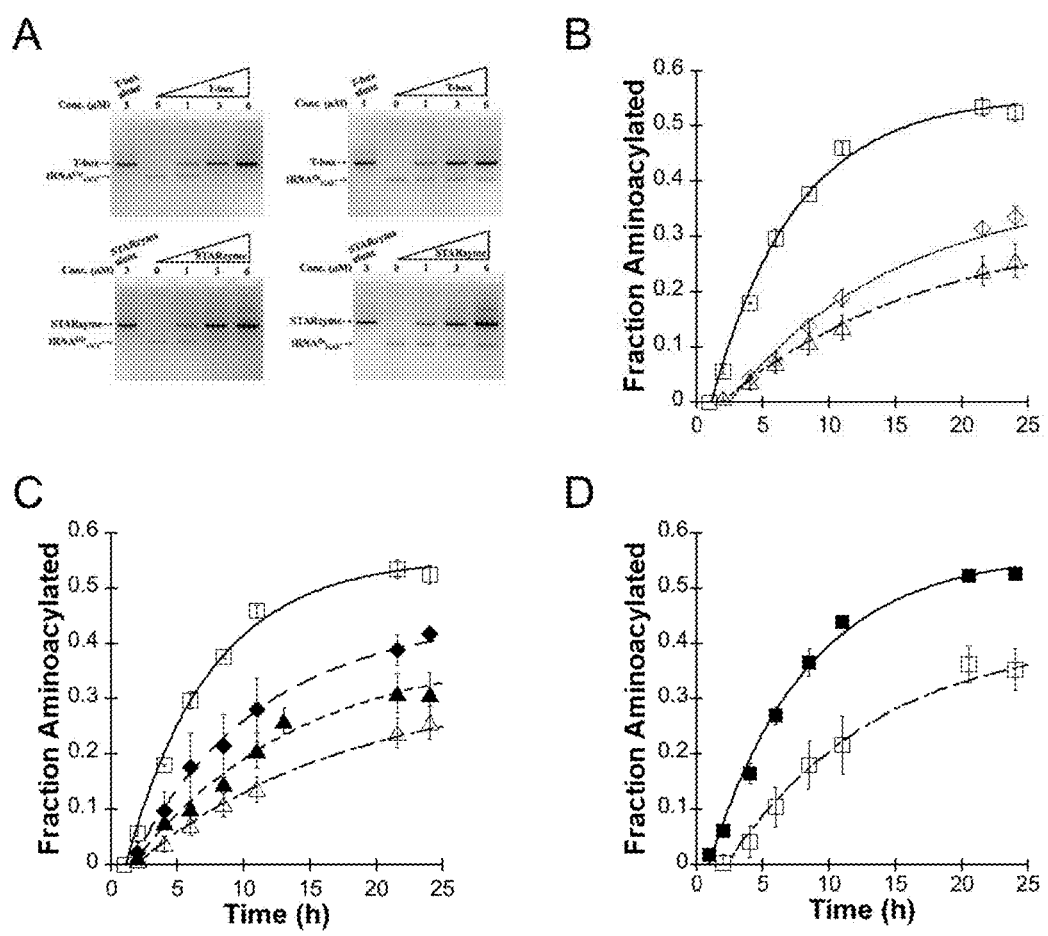
FIG. 9 shows the results of studies on the binding specificity and catalytic activity of at least one exemplary embodiment of the ribozyme of the present disclosure, with subpart (A) showing four in vitro gel shift assays representative of the results with those on the left showing that the increasing T-box RNA or STARzyme concentration ("STARzyme" described in additional detail below) correlates with the decreasing band intensity corresponding to tRNA$^{Gly}_{GCC}$, and the gels on the right showing that the band corresponding to the noncognate tRNA$^{Ile}_{GAU}$ did not change with T-box RNA or STARzyme; subpart (B) showing reaction progress curves for STARzyme (STAR-A8-minus1) against tRNA$^{Gly}_{GCC}$ U73A (open square), tRNA$^{Gly}_{GCC}$ (open diamond) or tRNA$^{Ile}_{GAU}$ mutant (open triangle); subpart (C) showing reaction progress curves for STARzyme against tRNA$^{Ile}_{GCU}$ (solid diamond) or tRNA$^{Ile}_{GCC}$ mutant (solid triangle) in comparison with tRNA$^{Gly}_{GCC}$ U73A mutant and tRNA$^{Ile}_{GAU}$; and subpart (D) showing reaction progress curves for STARzyme G88A against tRNA$^{Gly}_{GCC}$ U73A (open square) or tRNA$^{Gly}_{GUC}$ U73A (solid square) (error bars stand for standard deviations from three independent experiments)

As shown in FIG. 9, subparts (A)-(D), as compared to the wild-type tRNA$^{Ile}_{GAU}$, both mutants exhibited faster kinetics with about a 2-fold increase in $k_{obs}$ (see also Table 2 below). However, the rate and aminoacylation yield was noticeably lower than that seen with the cognate tRNA (FIG. 9, subpart (C): tRNA$^{Ile}_{GCU}$ (solid diamond), tRNA$^{Ile}_{GCC}$ mutant (solid triangle), tRNA$^{Gly}_{GCC}$ U73A (open square), tRNA$^{Ile}_{GAU}$ mutant (open triangle)). Accordingly, the specificity of the flexizyme 100 correlates well with the number of Watson-Crick base pairs between the tRNA anticodon loop 22 (three nucleotides) and the discriminator nucleotide 28 at position 73.

However, maximal activity was not observed with any of the tRNA$^{Ile}$ variants, even those that were fully complementary to the STARzyme 100 at their anticodon 22 and discriminator 28 positions. The data suggests that, as observed in the crystal structure of the T-box module 200 bound to tRNA 12, there are additional interactions between the elbow regions of tRNA$^{Gly}$ and the T-box module 200 of the flexizyme 100 that are not present when tRNA$^{Ile}$ is bound. This is also consistent with the lack of binding observed between the flexizyme 100 and the tRNA 12, which is an important features in the design of an effective orthogonal system.

TABLE 2

Kinetic parameters for STARzyme with GGC or GAC specifier sequence in the presence of a different tRNA constructs as indicated. Parameters reported here represents average values from three independent measurements. Errors stand for standard deviations.

| Specifier sequence | tRNA construct | Anticodon | $k_{obs}$ ($h^{-1}$) | $f_{max}$ |
|---|---|---|---|---|
| GGC | tRNA$^{Gly}_{GCC}$ U73A | match | 0.16 ± 0.0066 | 0.55 ± 0.0061 |
| GGC | tRNA$^{Ile}_{GAU}$ | mismatch | 0.047 ± 0.0094 | 0.40 ± 0.044 |
| GGC | tRNA$^{Ile}_{GCU}$ | match | 0.11 ± 0.041 | 0.47 ± 0.047 |
| GGC | tRNA$^{Ile}_{GCC}$ | match | 0.092 ± 0.025 | 0.38 ± 0.090 |
| GAC | tRNA$^{Gly}_{GCC}$ U73A | mismatch | 0.088 ± 0.022 | 0.43 ± 0.038 |
| GAC | tRNA$^{Gly}_{GUC}$ U73A | match | 0.14 ± 0.025 | 0.56 ± 0.022 |

Programming Specificity into the Flexizyme

Finally, the ability to change the anti-codon binding specifier region 426 of the T-box module 200 in affect a change in its specificity for a tRNA substrate 12 was assessed. A tRNA mutant was designed based on the body and structure of tRNA' (see FIG. 6). Perhaps more specifically, an anticodon 22 triplet of tRNA$^{Gly}_{GCC}$ A73U was mutated to GUC, which corresponds with an aspartate codon to generate the tRNA$^{Gly}_{GUC}$ mutant. Accordingly, the specifier trinucleotide 426 of tRNA$^{Gly}_{GCC}$ A73U was mutated from GGC to GAC (STARzyme G88A), which was complementary to the anticodon 22 triplet of the tRNA$^{Gly}_{GUC}$ A73U mutant.

Kinetic assays were performed to test if the ribozyme 400—and, in particular, the STARzyme G88A specifier mutant—had switched the specificity of the ribozyme 400 to favor tRNA$^{Gly}_{GUC}$ U73A over the cognate substrate. In the presence of the original tRNA$^{Gly}_{GUC}$ U73A construct, the STARzyme G88A mutant 400 reacted with a $k_{obs}$ value of 0.088±0.02 and results in a yield of about ~43%. (see FIG. 11, subpart (D), and Table 2). Both parameters were significantly lower than those obtained from the WT STARzyme 400, suggesting that it is necessary to have perfect complementarity between the anticodon 22 and the specifier 426 to achieve full aminoacylation activity. In the presence of the tRNA$^{Gly}_{GUC}$ U73A mutant, however, the STARzyme G88A mutant 400 reacts with a $k_{obs}$ value of 0.14±0.025 and $f_{max}$ is about 56%. Both parameters are the same, within errors, as those obtained from the WT ribozyme 400 in the presence of the original tRNA$^{Gly}_{GCC}$ U73A construct. Accordingly, the data suggest that it is possible to change the specificity of the ribozyme 400 for its tRNA substrate 12 in a predictable manner.

Materials and Methods

The various materials and methods used for preparing the variants and performing the studies described herein are as follows and are additionally well known in the art:

RNA Sample Preparation. DNA oligos for PCR reactions were ordered from IDT. DNA templates for ribozymes 300, 400 and tRNAs were inserted into pUC-19 between the XbaI and HindIII restriction sites. RNA samples were made by in vitro transcriptions, and purified by urea denaturing gel electrophoresis as previously described.

In vitro gel shift assays. tRNA, the antiterminator-deleted glyQS T-box RNA, and STARzyme samples were diluted into 10 µM stocks in 50 mM HEPES-KOH (pH 7.5) and 100 mM KCl. To refold, RNA samples were heated separately at 95° C. for about 2 min, and slowly cooled to room temperature over about 10 min. Thereafter, 10 mM of $MgCl_2$ was added to the sample followed by an additional 5-min incubation at room temperature. 0, 1, 3 or 6 µM of the refolded T-box RNA or STARzyme were mixed with 1 µM of refolded tRNA samples in the presence of 50 mM HEPES-KOH pH 7.5, 100 mM KCl and 10 mM $MgCl_2$. The 20-µL binding reactions were incubated at room temperature for 30-60 min followed by the addition of 5 µL 50% glycerol. 5 µL of the samples (out of 25 µL) were then loaded onto a 6% native polyacrylamide gel (0.5×Tris/borate/EDTA buffer, 5 mM $MgCl_2$). The gel was run at 4° C. at 10 W for 1.5 hour. The gel was stained with Stains-all (Sigma) overnight at 4° C. Gel images were obtained using Bio-Rad ChemiDoc XRS+.

Single-turnover kinetics. 10 µM of ribozyme and 2 µM of tRNA sample were heated separately at 95° C. for 2 min in a buffer containing 50 mM pH 7.5 HEPES-KOH and 100 mM KCl. Samples were slowly cooled to room temperature over 10 min. 20 mM $MgCl_2$ was then added to each sample, followed by ~10 min incubation at room temperature. The ribozyme 300, 400 was then mixed with tRNA and the reaction solution was incubated at room temperature for about 1 h. Reaction solution was then incubated at 4° C. for 10 min.

To start the reaction, 5 mM DBE-activated alkynyl amino acid substrate was added. At each time point, 2 µL of the reaction aliquot was removed and quenched with 8 µL of acid loading dye that contains 100 mM sodium acetate pH 5.2, 7 M urea, 0.05% bromophenol blue and 10 mM EDTA. Reaction products were resolved by 8% acidic denaturing (7 M urea) gel buffered with 100 mM sodium acetate pH 5.2. The gel was stained with SYBR Green II (Life technologies). Fluorescent signal was detected using Typhoon FLA 9500 (GE Healthcare), and the intensity of fluorescence over time was measured using ImageQuant TL (GE Healthcare). Rate constants were obtained by fitting the fraction of aminoacylated tRNA versus time using the single-exponential equation (Synergy KaleidaGraph V4.1):

$$f_t = f_0 + (f_{max} - f_0)(1 - e^{-k_{obs}t}),$$

where $f_t$ is the fraction of tRNA charged at time t, $f_0$ is the fraction of tRNA charged at time zero that corrects for the background noise due to insufficient separation between the charged and uncharged tRNA (see FIG. 11 for detail), $f_{max}$ is the fraction of tRNA charged at infinite time and was used in this paper to represent maximal aminoacylation yield, $k_{obs}$ is the first-order rate constant.

Labelling aminoacylated tRNA with a fluorophore. Two 20-µL aminoacylation reactions containing 10 µM of ribozyme and 2 µM of tRNA sample were prepared and initiated as described above for the activity assays. The reactions were incubated at 4° C. for about 6 hours (dFx) or about 24 hours (STARzyme) to achieve maximal aminoacylation yield of the tRNA. After the incubation, the RNA was precipitated by the addition of 40 µL of 0.3 M pH 5.2 sodium acetate and 100-µL of room temperature ethanol. RNA samples were spun down by centrifugation at 4° C. for 25 min at 13,200 rpm. The pellet was washed twice with 20-µL, of 70% ethanol containing 0.1 M NaCl, followed by brief centrifugation. Copper-catalyzed click reactions were performed using a Click-iT Plus Alexa Fluor 488 Picolyl Azide Toolkit (ThermoFisher Scientific).

Briefly, a 500-µL reaction cocktail containing 5 µM of Alexa Fluor 488 picolyl azide and 10 µL of the provided copper protectant was prepared following the manufacture's protocol. No $CuSO_4$ was added to the cocktail to minimize RNA degradation. The precipitated RNA pellet was then dissolved in 20 µL of the reaction cocktail. The click reaction was incubated in dark for 30 min. In order to remove the "unclicked" azide, the 20-µL, click reaction was diluted into 500-µL by adding 480-µL, of 100 mM sodium acetate at pH 5.2. The 500-µL, solution was then concentrated to ~20-µL by using an Amicon Ultra centrifugal filter unit with a 10 K NMWL cutoff. The process was then repeated once to further remove any residual azide. The click reaction sample was then mixed with equal volume of colorless acid loading buffer that contains 100 mM sodium acetate pH 5.2, 7 M urea, 0.05% and 10 mM EDTA. Gel electrophoresis was performed as described in the above section. To analyze the click reaction product, unstained gels were scanned using Typhoon FLA 9500 (GE Healthcare).

Figure 10:
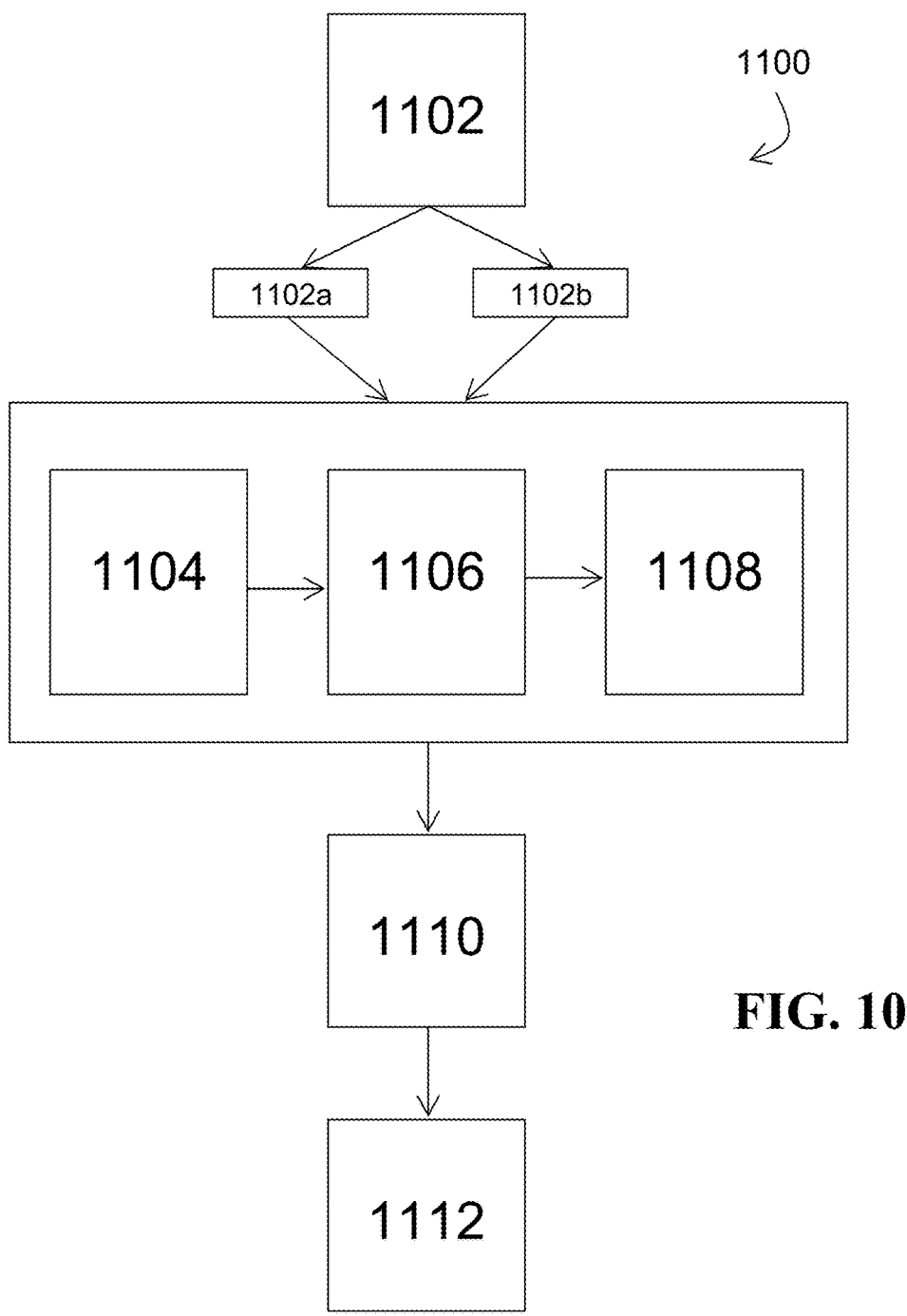
FIG. 10 shows a flow-chart representative of at least one embodiment of a method for engineering and/or producing the ribozyme of FIG. 4A.

Methods for engineering, producing, and using the inventive fusion ribozymes described herein are also a feature of the present disclosure. Now referring to FIG. 10, a flowchart illustrative of a method 1100 for engineering and/or producing a ribozyme 400 is shown. At step 1102, a starting molecule is created by fusing a flexizyme module 100 (to facilitate acceptance of a wide variety of amino acid substrates) with a tRNA-specific T-box module 200 (to create specificity for the tRNA). In at least one exemplary embodiment of the method 1100, the flexizyme module 100 comprises dFx and the T-box module 200 comprises a Gkau glyQS T-box.

Depending on the desired structure of the ribozyme 400, in at least one exemplary embodiment of the method 1100, step 1102 may comprise either sub-step 1102a or 1102b. Perhaps more specifically, where a linear fusion ribozyme 400 is desired, at sub-step 1102a, the 3'-terminus of the T-box module 200 is connected to the 5'-terminus of a flexizyme module 100 via a 5 to 10 nucleotide poly-A linker 450 with the secondary structure presenting within both modules 100, 200 following the fusion at sub-step 1102a. This creates a linear permutation of the ribozyme 400.

Alternatively, if a circularly permuted topology of the flexizyme is desired, step 1102 may comprise linking the 3'-terminus of the T-box module 200 to the 5'-terminus of a flexizyme module 100 and opening the P1 loop of the flexizyme 100 at sub-step 1102b. To maximize functionality, sub-step 1102b may optionally comprise the incorporation of one or more adenosines to facilitate the linkage between the 5'-terminus of the parental flexizyme 100 and the 3'-terminus of the T-box RNA 200 that comprises the CCA-binding site 419 of the flexizyme. In this embodiment, the 3'-terminus of the T-box module 200 may then be connected to the new 5'-terminus of the circularly permuted flexizyme 100.

At step 1104, cognate tRNA 12 is bound to the T-box module 200 and, at step 1106, tRNA 12 is bound to the flexizyme module 100. For example, in at least one exemplary embodiment, at step 1104 the anticodon 22 of the tRNA 12 binds the specifier loop 426 of the leader portion 24 of the T-box RNA 200 and, at step 1106, the acceptor end 27 (3'-terminus) of the bound tRNA 12 is superposed over the acceptor stem analog 417 present in the crystal structure of the flexizyme 100. As the T-box 200 exhibits tRNA specificity, the ribozyme 400 will only allow tRNA 12 it specifically recognizes (cognate) to bind. Further, at step 1108, an amino acid (e.g., a uAA) is bound to the active site 418 of the flexizyme 100.

It will be appreciated that steps 1104, 1106, and/or 1108 may be performed concurrently or in any order or sequence. Furthermore, at least steps 1104 and 1108 may be performed before or after step 1102, as desired. It will be appreciated that the tRNA 12 and/or an amino acid 14 may be bound with the ribozyme 400 (or any component thereof) at any point within the method 1100 or thereafter.

In at least one embodiment, method 1100 may further comprise optimization step 1110. As previously described, the interplay between the flexizyme module 100 and the T-box module 200 of the ribozyme 400 may be engineered to achieve optimal catalytic activity and/or improved specificity (e.g., through in vitro evolution by randomly introducing mutations into the ribozyme 400 and selecting for those that have the highest activity and strongest selectivity for cognate tRNA). This may be achieved in a number of ways, for example, by changing the length of the P1 stem of the flexizyme 100 and/or the size of the linker 450. Accordingly, at step 1110, compensatory mutations may be introduced to the CCA tail 16 of the tRNA 12 and/or internal guide, base pairs may be added to or removed from P1 stem (e.g., removing one A•U base pair therefrom), and/or the number of nucleotides present within the linker 450 of a circularly permuted flexizyme 100 molecule may be optimized (e.g., the linker 450 may be engineered to comprise eight (8) nucleotides).

Additionally or alternatively, the ribozyme 400 may be further manipulated to alter the tRNA substrate 12 specificity thereof at step 1112. For example, the anti-codon binding specifier loop 426 of the ribozyme 400 may be modified to change its specificity for a tRNA substrate 12. It will be appreciated that the specifier loop 426 may be modified as desired provided that it is complementary to the anticodon triplet 22 of the desired cognate tRNA 12. Accordingly, step 1112 allows for the specificity of the ribozyme 400 for its desired cognate tRNA substrate 12 to be modified in a predictable and effective manner. Notwithstanding the foregoing, it is notable that the substrate specificity of the ribozyme 400 with respect to an amino acid substrate 14 need not be manipulated as the flexizyme module 100 does not discriminate between amino acids 14 and can thus charge a bound tRNA 12 with any desired amino acid 14—even if that amino acid 13 is an uAA.

Figure 11:
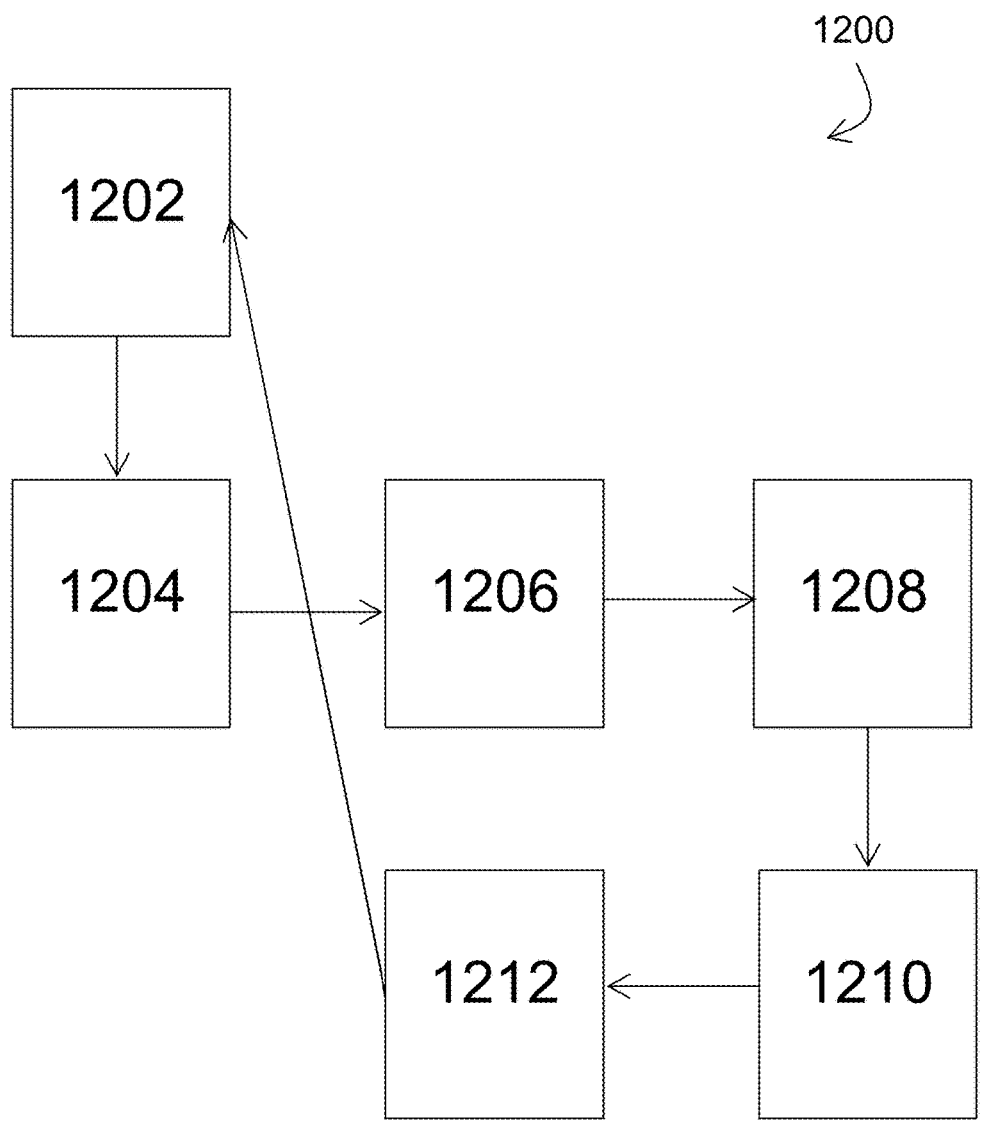
FIG. 11 shows a flow-chart representative of at least one embodiment of a method for incorporating an unnatural amino acid into a growing polypeptide chain (i.e. a protein) using the ribozyme of FIG. 4A.

Now referring to FIG. 11, a method 1200 of incorporating a uAA into a growing polypeptide chain using the ribozyme 400 hereof is also provided. Such method 1200 may be performed in vivo in a cell (e.g., a non-eukaryotic cell, such as an *E. coli* cell or the like, or a eukaryotic cell) and/or in in vitro applications, as desired. For the avoidance of doubt, as used herein, the term "cell" shall refer to and mean either an in vivo or in vitro application unless expressly indicated otherwise. Method 1200 enables the synthesis of proteins that comprise uAAs in large and useful quantities, which is exceedingly beneficial due to the number of important applications for proteins that include uAA(s).

Generally, the incorporation of a uAA into a protein can be done to tailor changes in the protein structure and/or function, such as, for example, to change its size, acidity, nucleophilicity, hydrogen bonding, hydrophobicity, accessibility of protease target sites, target to a moiety (e.g., for a protein array), etc. Furthermore, proteins that include a uAA can have enhanced or even entirely new catalytic or physical properties (e.g., toxicity, structural properties, biodistribution, chemical and/or photochemical properties, spectroscopic properties, catalytic ability, half-life, ability to react with other molecules (e.g., covalently or noncovalently), and the like). As such, the compositions including such proteins are useful in a vast number of contexts including, for example, for novel therapeutics, diagnostics, industrial enzymes, catalytic enzymes, binding proteins (e.g., antibodies), as well as in the study of protein structure and function. Additionally, one or more uAAs may be incorporated into a polypeptide to provide a molecular tag.

As previously described, the ribozyme 400 comprises a single molecule that includes a discriminating binder element (i.e. the T-box module 200) capable of binding a cognate tRNA 12 with specificity, an indiscriminate amino acid 14 binder element (i.e. the active site 418 of the flexizyme module 100), and an ARS-like catalyzing element for catalyzing the addition of an amino acid 14 to a tRNA 12 substrate (i.e. the flexizyme module 100). The ribozyme 400 can be used in connection with a translation system (either in vivo or in vitro) to incorporate a uAA 14 into a protein.

At step 1202 of the method 1200, the ribozyme 400 and the desired substrates 12, 14 are delivered to a cell. Because the ribozyme 400 is an RNA molecule, the ribozyme 400 can be delivered to the cell on a single plasmid along with its suppressor tRNA and amino acid substrates 12, 14. Furthermore, if introduced into a living cell, use of the ribozyme 400 bypasses the need to translate the catalyst component into a protein. As is known in the art, the specific cognate tRNA 12 chosen will coincide with the specialized codon within the mRNA (e.g., an amber STOP codon) positioned at the location where the uAA 14 is to be incorporated within the polypeptide chain. Additionally, it will be appreciated that the ribozyme 400 may be used in place of—or in conjunction with conventional orthogonal systems At step 1204, the ribozyme 400 binds the suppressor tRNA 12 and, at step 1206, charges the bound tRNA 12 with the uAA 14. Namely, at step 1204, the specifier loop 426 of the T-box module 200 binds the anticodon 22 of the tRNA 12 (with specificity) and the acceptor end 419 of the flexizyme module 100 binds the CAA tail 16 of the bound tRNA 12. Due to the specificity provided by the T-box module 200, the ribozyme 400 specifically recognizes and aminoacylates its targeted suppressor tRNA 12 without the risk of crosstalk with any endogenous tRNA (or synthetases) present (within a living cell or otherwise).

Further, at step 1206, the active site 418 of the flexizyme module 100 binds the uAA 14. Note that the active site 418 of the flexizyme module 100 exhibits high substrate promiscuity with respect to amino acid substrates 14 and will thus will have a high degree of effectiveness in binding (and using in connection with aminoacylation) most amino acid substrates 14 added to the cell.

The ribozyme 400 catalyzes aminoacylation of the bound tRNA substrate 12 at step 1208. Perhaps more specifically, the flexizyme module 100 of the ribozyme 400 adds the bound uAA 14 to the bound tRNA substrate 12, thereby charging the tRNA 12 and releasing the same from the ribozyme 400. At step 1210, the charged tRNA 12 is transferred to the ribosome and used in ribosomal translation.

If, during the method 1200, a change in amino acid substrate 14 is desired, the method 1200 may advance to step 1212, where the new substrate 14 is simply added to the cell. Indeed, because the flexizyme module 100 (i.e. catalytic component) of the ribozyme 400 can accommodate a wide variety of amino acid substrates 14 at its active site 418, in most cases, it need not be reengineered if a different substrate 14 is to be used. Indeed, the new substrate 14 can simply be added the method 1200 will repeat, using the new amino acid 14.

Accordingly, unlike conventional techniques, the compositions and methods of the present disclosure provide a streamlined and easy-to-use process for incorporating uAAs into protein biosynthesis. While various embodiments of compositions, systems, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to he defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. An artificial ribozyme comprising:
   a T-box element comprising a 3'-terminus and a riboswitch element having a specifier loop for binding a cognate tRNA substrate with specificity; and
   a flexizyme comprising SEQ ID NO: 2, which defines at least an active site for binding an unnatural amino acid, an acceptor end for base pairing to a terminus of a tRNA substrate, a nucleotide linker, and a P1 stem linked to the 3'-terminus of the T-box element,
   wherein when the T-box element recognizes and preferentially binds the cognate tRNA substrate, the flexizyme can bind and aminoacylate the cognate tRNA substrate bound by the T-box element, and the active site of the flexizyme is not specific to a targeted unnatural amino acid.

2. The artificial ribozyme of claim 1, wherein the T-box element comprises a bacterial T-box element derived from a Geobacillus kaustophilus and the flexizyme comprises a dinitro-flexizyme.

3. The artificial ribozyme of claim 1, wherein the 3'-terminus of the T-box element and a 5'-terminus of the flexizyme are connected via a poly-A linker comprising between five and ten nucleotides.

4. The artificial ribozyme of claim 3, comprising SEQ ID NO: 1.

5. The artificial ribozyme of claim 1, wherein a 5'-terminus of the T-box element further comprises a guanine-adenine-guanine nucleotide sequence linked thereto to facilitate in vitro transcription of the artificial ribozyme.

* * * * *